US007309858B2

(12) United States Patent
Pappin et al.

(10) Patent No.: US 7,309,858 B2
(45) Date of Patent: Dec. 18, 2007

(54) METHOD AND APPARATUS FOR DE-CONVOLUTING A CONVOLUTED SPECTRUM

(75) Inventors: Darryl J. C. Pappin, Boxborough, MA (US); Nikita Khainovski, Framingham, MA (US); Darryl D. Spencer, Framingham, MA (US)

(73) Assignee: Applera Corporation, Foster City, CA (US)

( * ) Notice: Subject to any disclaimer, the term of this patent is extended or adjusted under 35 U.S.C. 154(b) by 0 days.

(21) Appl. No.: 11/458,082

(22) Filed: Jul. 17, 2006

(65) Prior Publication Data

US 2007/0023634 A1 Feb. 1, 2007

Related U.S. Application Data

(62) Division of application No. 10/916,629, filed on Aug. 12, 2004, now Pat. No. 7,105,806.

(60) Provisional application No. 60/524,884, filed on Nov. 26, 2003, now abandoned.

(51) Int. Cl.
*G01N 33/00* (2006.01)

(52) U.S. Cl. .......................... 250/282; 436/173; 435/6

(58) Field of Classification Search ..................... None
See application file for complete search history.

(56) References Cited

U.S. PATENT DOCUMENTS

| | | | | |
|---|---|---|---|---|
| 6,524,803 | B2 * | 2/2003 | Overney et al. | 435/7.1 |
| 6,940,065 | B2 * | 9/2005 | Graber et al. | 250/282 |
| 6,962,818 | B2 * | 11/2005 | Schneider et al. | 435/6 |
| 2002/0106648 | A1 * | 8/2002 | Lizardi et al. | 435/6 |
| 2002/0192708 | A1 | 12/2002 | Steen et al. | |
| 2005/0061967 | A1 * | 3/2005 | Shvartsburg et al. | 250/288 |
| 2005/0153456 | A1 * | 7/2005 | Pappin | 436/166 |
| 2005/0226591 | A1 * | 10/2005 | Hur et al. | 702/19 |

OTHER PUBLICATIONS

Eugster, O., et al., Identification of Isobaric Interferences. A Computer Program For Ion Microprobe Mass Spectral Data, International Journal of Mass Spectrometry and Ion Processes (1985) 66:291-312, Elsevier Science Publishers B.V., Amsterdam—Printed in The Netherlands.

Kushnir, Mark M., et al., Simultaneous quantitative analysis of isobars by tandem mass spectrometry from unresolved chromatographic peaks, ARUP Institute for Clinical and Experimental Pathology, Journal of Mass Spectrometry (2004) 39: 532-540, Wiley InterScience (www.interscience.wiley.com) DOI:10.1002/jms.619.

Simultaneous quantitative analysis of isobars by tandem mass spectrometry from unresolved chromatographic peaks, Mark M. Kushnir, Alan L. Rockwood and Gordon J. Nelson, ARUP Institute for Clinical and Experimental Pathology, Journal of Mass Spectrometry (2004) 39: 532-540.

Identification of Isobaric Interferences. A Computer Program For Ion Microprobe Mass Spectral Data, International Journal of Mass Spectrometry and Ion Processes (1985) 66:291-312.

* cited by examiner

*Primary Examiner*—Jack I. Berman
(74) *Attorney, Agent, or Firm*—Miles & Stockbridge P.C.; David R. Schaffer

(57) ABSTRACT

Embodiments of the present invention relate to methods, systems, and apparatus suitable for performing a survey scan of one or more analytes or labeled fragments of analytes to obtain a convoluted spectrum and to de-convolute the convoluted spectrum using, for example, a mass spectrometer and associated processing system.

28 Claims, 12 Drawing Sheets

Table 1

| Mass (Daltons) | 114 | 115 | 116 | 117 |
|---|---|---|---|---|
| | | | | |
| Main Peak | | 8.7 | 6.2 | |
| Down Mass Side Peak | 0.5 | 0.3 | | |
| Up Mass Side Peak | | | 1.0 | 0.6 |
| Convoluted Spectrum | 0.5 | 9.0 | 7.2 | 0.6 |
| Normalized Intensity | | 10.2 | 7.1 | |
| Ratio 115 | 0.049 | 0.853 | 0.098 | |
| Ratio 116 | | 0.042 | 0.873 | 0.085 |

METHOD AND APPARATUS FOR DE-CONVOLUTING A CONVOLUTED SPECTRUM

CROSS-REFERENCE TO RELATED APPLICATION

This application is a Divisional of and claims benefit of priority to U.S. Non-Provisional patent application Ser. No. 10/916,629, filed Aug. 12, 2004, now U.S. Pat. No. 7,105,806 allowed, which claims benefit of priority to U.S. Provisional Patent Application Ser. No. 60/524,884, filed Nov. 26, 2003, now abandoned, both of which are herein incorporated in their entireties by reference.

FIELD OF THE INVENTION

Embodiments of the present invention relate to the analysis of spectral data.

INTRODUCTION

In some embodiments the invention pertains to methods and systems for de-convoluting (e.g., normalizing) a convoluted spectrum to obtain normalized peak intensity values that can be useful for qualitative and/or quantitative analysis. For example, these normalized peak intensity values can be correlated with labels (e.g., isotopically enriched labels and/or labeling reagents, such as, those described in U.S. patent application Ser. No. 10/765,458, herein incorporated in its entirety by reference) used to mark analytes for their qualitative and/or quantitative determination. A convoluted spectrum can be a multiple component spectra, obtained for a defined spectral region, which comprises overlapping isotopic clusters. A convoluted spectrum can be obtained by mass analysis of the overlapping isotopic clusters wherein each isotopic cluster defines a label, a fraction or part of a label and/or a labeled analyte.

In some embodiments, the convoluted spectrum can be compiled from output data obtained from an analyzer such as a mass spectrometer. In addition to the de-convoluted spectrum, ratio information can be provided for each isotopic cluster. By ratio information, we mean the relative intensity of each of the peaks that define an isotopic cluster. Given the convoluted spectrum and the ratio information, it is possible to determine the intensity of a main peak and the one or more up-mass and the one or more down-mass side peaks that define each isotopic cluster. For the purpose of qualitative and/or quantitative analysis, it is also possible to determine the normalized peak intensity attributable to each entire isotopic cluster. Because the normalized peak intensity for the isotopic cluster can be determined, and because the isotopic cluster can define a particular label, a fraction or part of a label and/or a labeled analyte, the normalized peak intensity can be used for both qualitative and/or quantitative determinations of the label and/or the analyte in one or more samples subjected to analysis by the analyzer.

In some embodiments of the present invention, the convoluted spectrum defines a spectral region of interest where isotopic clusters can be generated by the fragmentation of isobaric and/or isomeric labeling reagents. The fragmentation of the isomeric and/or isobaric labeling reagents can occur by subjecting the label and/or the labeled analyte to dissociative energy levels (e.g., collision-induced dissociation (CID)). The normalized peak intensity for each isotopic cluster can correlate with the presence and/or quantity of label that produces the isotopic cluster that in turn can correlate with the presence and/or quantity of an analyte. The various isotopic clusters that define the convoluted spectrum can each be attributable to a different label or a different labeled analyte. The labels and/or labeled analytes can be obtained from the same or from different samples. In some embodiments, two or more samples comprising labeled analytes are mixed wherein each sample is labeled with a different isotopic labeling reagent of a set of isotopic labeling reagents. Accordingly, the analysis of the convoluted spectrum can be used in the qualitative and/or quantitative analysis of one or more analytes in one or more samples. In some embodiments, reporter ions of the labeling reagent and daughter fragment ions can be produced in the same energy scan in the analyzer. This can permit, from the same energy scan, the determination of the analyte that produces the daughter fragment ions as well as relative and/or absolute quantitative determination of that analyte in two or more samples mixed to form a sample mixture that was analyzed.

The process of de-convoluting the convoluted spectrum can proceed in many different ways. For example, the convoluted spectrum can be considered the sum of wave functions, each of which defines one isotopic cluster of the plurality of isotopic clusters. The convoluted spectrum can also be viewed as the sum of a plurality of isotopic clusters, each isotopic cluster being defined as a wave function that represents a plurality of peaks; with each peak having a certain peak intensity. Regardless of how the convoluted spectrum is de-convoluted, the analysis can be viewed as a process of starting with output peak intensity data (e.g., summary peak intensity data) for each isotopic cluster in the convoluted spectrum followed by the addition, inclusion or combination of peak intensities associated with each isotopic cluster and the subtraction or removal of peak intensities not-associated with each isotopic cluster. In some embodiments, removal of contributions from the peaks of neighboring isotopic clusters and compensation due to side peaks of the main summary peak can be effected by blind deconvolution or parameter-free methods that one skilled in the art will appreciate. In this way, it is thereby possible to determine a normalized peak intensity that corresponds with each isotopic cluster. As a result, it is possible to assign a single quantitative value to each isotopic cluster based upon the analysis of the convoluted spectrum.

When the analysis is performed using wave functions, the transition from summary peak intensities to normalized peak intensities can involve the simultaneous addition and subtraction of peak intensities by the analysis of wave functions. For these calculations, the summary peak intensities can be viewed as a wave function that defines the entire isotopic cluster. When the analysis is performed by other methods, the summary peak intensities can be viewed as output peak intensities. In this case there can be discrete addition and subtraction of peak intensities as well as assigned temporary peak intensities in a manner that proceeds to associate the peak intensities with a particular isotopic cluster to thereby produce the normalized peak intensities for the isotopic cluster.

In accordance with some embodiments of the present invention, the compounds used as labeling reagents that can produce the isotopic clusters can be centered in “quiet zones” across the mass spectrum. For example, the “quiet zones” can be determined by measuring intensity information for a large number of analytes, such as peptides, summing the results and determining the “quiet zones” from the summed result. The “quiet zones” are areas where there is little or no mass information observed in the summed result for the selected analyte. By directing the analysis of the isotopic clusters to "quiet zones" based upon a judicious choice of labeling reagents and isotopic enrichment processes (or synthesis strategies using enriched starting materials) it is possible to minimize background noise that can interfere with the accuracy of quantitative analysis. Choosing the labeling reagents so that daughter fragment ions generated therefrom are centered in the "quiet zones" can also aid in the collection of the reporter and daughter fragment ions in the single energy scan in the analyzer because there is little or no overlap between fragments associated with an analyte (i.e., daughter fragment ions) and fragments associated with the labeling reagent (i.e., reporter ions).

DESCRIPTION OF VARIOUS EMBODIMENTS OF THE INVENTION

Figure 1:
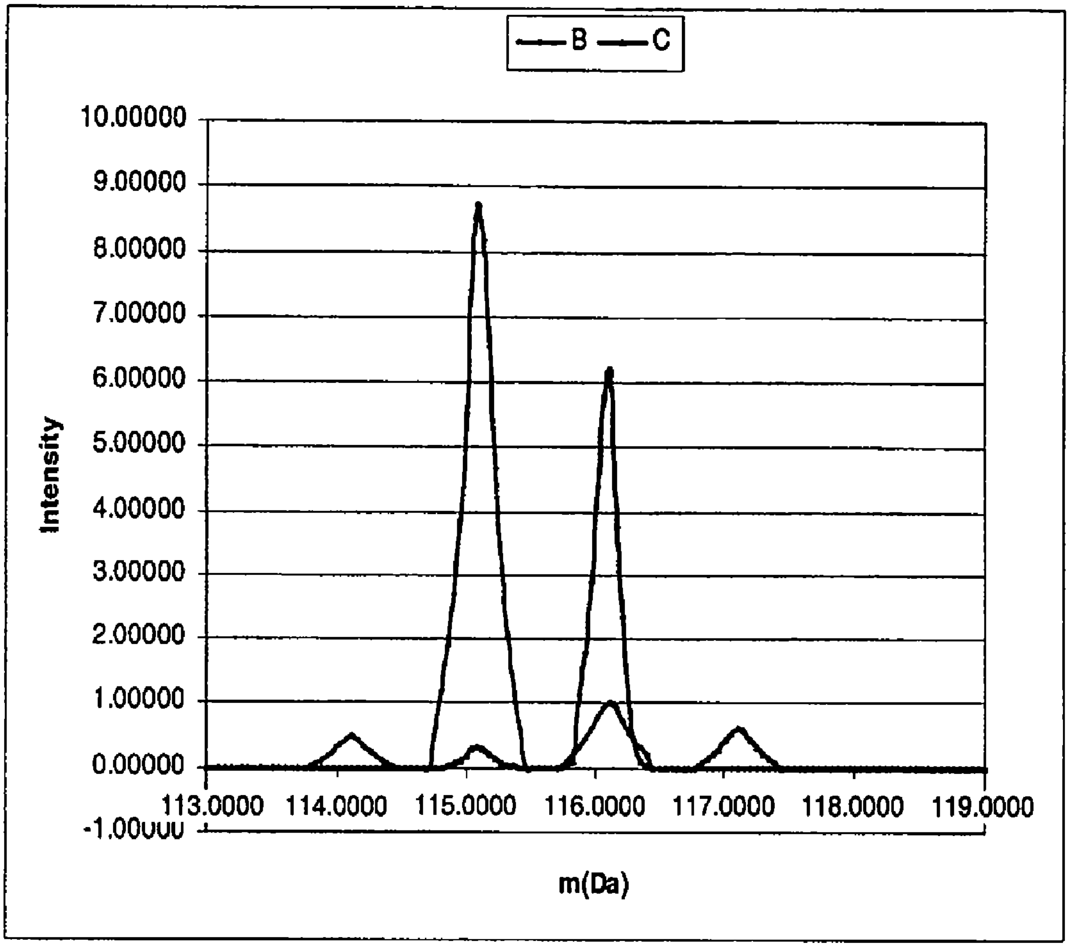
FIG. 1 is a color illustration of a simple model of two overlapping isotopic clusters and a Table that provides information about certain features of the illustration.

For the purposes of interpreting this specification, the following definitions will apply and whenever appropriate, terms used in the singular will also include the plural and vice versa. The definitions set forth below shall supercede any conflicting definitions in any documents incorporated herein by reference.

As used herein, "label" refers to a moiety suitable to mark an analyte for determination. The term label is synonymous with the terms tag and mark and other equivalent terms and phrases. For example, a labeled analyte can be referred to as a tagged analyte or a marked analyte. Labels can be used in solution or can be used in combination with a solid support.

As used herein an "isotopic cluster" refers to a grouping of intensity peaks associated with a single compound (e.g., a label or labeled analyte), where the compound that forms the isotopic cluster can be isotopically enriched. The isotopic cluster can include a single main peak (or main isotope peak) and two or more side peaks. The side peaks are generally of lower intensity than the main isotope peak, and can be both down-mass and up-mass of the main isotope peak. Although the separation between the main peak and side peaks can be measured in whole numbers, for example, 1, 2, 3, etc. Daltons ("Da"), the separation may also be measured as non-whole numbers, for example, 0.5, 1.2, etc. For example, an isotopic cluster with a main peak at X Da can include the intensity contribution of an up-mass side peak at X+1 Da and the intensity contribution of a down-mass side peak at X−1 Da.

As used herein, "isotopically enriched" refers to a compound (e.g., label, labeling reagent or labeled daughter fragment ion) that has been enriched synthetically with one or more high mass isotopes (e.g., stable isotopes such as Deuterium, $^{13}C$, $^{15}N$, $^{18}O$, $^{37}Cl$ or $^{81}Br$). By "enriched synthetically" we mean the application of processes that introduce high mass isotopes into a compound in excess of the natural isotopic abundance. Because isotopic enrichment is not 100% effective, there can be impurities of the compound that are of lesser states of enrichment and these will have a lower mass. Likewise, because of over-enrichment (undesired enrichment) and because of natural isotopic abundance, there can be impurities of greater mass. This is why a sample of a single isotopically enriched compound (or part thereof) can, when subjected to analysis in a mass spectrometer, produce an isotopic cluster of daughter fragment ions having both at least one up-mass side peak and at least one down-mass side peak in addition to the main peak attributable to the majority of the compound.

As used herein, "natural isotopic abundance" refers to the level (or distribution) of one or more isotopes found in a compound based upon the natural prevalence of an isotope or isotopes in nature. For example, a natural compound obtained from living plant matter will typically contain about 0.6% $^{13}C$.

Similarly, as used herein, "intensity" refers to the height of, or area under, a peak. For example, the peak can be output data from a measurement occurring in a mass spectrometer (e.g., as a mass to charge ratio (m/z)). In accordance with some embodiments of the present invention, intensity information can be presented as a maximum height of the summary peak or a maximum area under the summary peak representing a mass-to-charge ratio.

As used herein, a "convoluted spectrum" is output data, or a portion thereof, from an analyzer. A convoluted spectrum can combine intensities from one or more different isotopic clusters. In other words, the convoluted spectrum can include the result of combining the peak intensities of two or more overlapping isotopic clusters. The convoluted spectrum can comprise other spectral data but can also be chosen to exist in a "quiet zone" as described herein. Thus, the convoluted spectrum can comprise the entirety of output data from an analyzer or can comprise only the selected information or data associated with the peak intensities of the overlapping isotopic clusters to the exclusion of other spectral data that might be output from an analyzer such as a mass spectrometer. Where the convoluted spectrum contains information other than the combined intensity data for two or more isotopic clusters as background noise within the spectral area of interest, a suitable correction can be made to eliminate the contribution of such information.

As used herein, "main summary isotope peak" refers to a peak observed in a convoluted spectrum that is the main peak of an isotopic cluster. The main peak of the isotopic cluster is the peak of the isotopic cluster with the largest intensity. In some embodiments, the peak intensity of the "main summary isotope peak" can be the output intensity for the main peak of the isotopic cluster determined from the convoluted spectrum. In some embodiments, the peak intensity for the "main summary isotope peak" can be the accumulated peak intensity for all those intensity peaks associated with an isotopic cluster. In some other embodiments, the peak intensity of the "main summary isotope peak" can be the wave function for the output intensity for the isotopic cluster defined by the main peak and its one or more up-mass and down-mass side peaks.

As used herein "summary peak intensity" refers to the intensity of a single peak in the output peak intensity data of a convoluted spectrum or can refer to a peak intensity that combines the intensity of a single main peak with the intensities of one or more other associated side peaks of the isotopic cluster. Summary peak intensity data is output peak intensity data.

As used herein, "known peak intensity" refers to the known intensity for a peak associated with an isotopic cluster. The known peak intensity can be known because it is experimentally determined or it can be known because it has been calculated from the analysis of experimental data. For example, the known peak intensity can be a peak intensity for the main peak or the peak intensity for an up-mass side peak or a down-mass side peak. Known peak intensity can also be known for an isotopic cluster where the isotopic cluster can be defined by a model (for the ratios), a wave function or matrix. In some embodiments, known peak intensity data can be determined experimentally from relative ratio information for the peaks of an isotopic cluster. In some embodiments, known peak intensity data can be determined using blind de-convolution.

As used herein "temporary peak intensity" refers to a transitory peak intensity assignment that can be used when calculating a normalized peak intensity from summary peak intensity data. There can be more than one temporary peak intensity assignment for each calculation.

As used herein, "normalized intensity" or "normalized peak intensity" refers to the accumulated peak intensities of a single compound associated with an isotopic cluster (e.g., the main peak and all associated side peaks). For example, the normalized peak intensity for a main summary isotope peak is the accumulated peak intensity for the peaks associated with an isotopic cluster. In a de-convoluted spectrum, "normalized peak intensity" for the isotopic cluster at X Da can be defined to contain the intensity contribution of the main isotope peak (e.g., at X Da) plus the intensity contributions of one or more down-mass side peaks (e.g., at X−1 Da, X−2 Da, X−3 Da, etc.) and one or more up-mass side peaks (e.g., at X+1 Da, X+2 Da, X+3 Da, etc.) for the single isotopic cluster formed by the compound (i.e., fragment ions associated with a reporter) to the exclusion of peak intensity components of other compounds (i.e., fragment ions associated with another reporter).

Each isotopic cluster can include a main isotope peak intensity as well as an up-mass side peak intensity and a down-mass side peak intensity. The main isotope peak of the isotopic cluster can be centered on a single mass value, for example 115 Da, and the side peak intensities, generally, can be centered on different mass values above and below the main isotope peak. In some embodiments, there can be two or more side peaks centered around a mass value of one or more mass units more or less than the main peak mass. For example, in some other embodiments, the isotopic cluster can be centered around 115 Da with a separation of a single Dalton between peaks, the down-mass side peaks being centered around 114 Da, 113 Da, 112 Da, etc., and the up-mass side peaks being centered around 116 Da, 117 Da, 118 Da, etc. Of course, as the side peaks move progressively away from the main peak, the size of each side peak can begin to diminish, that is, approach zero. Accordingly, side peaks that have a nominal intensity (e.g., less than from about 0.1% to about 0.5% of the main peak intensity of the isotopic cluster) have such a small effect that in some embodiments it is not worth considering the intensity contributions from these peaks. The ordinary practitioner can determine the degree of scrutiny to be applied to the up-mass and down mass side peaks depending upon the application and the degree of accuracy required.

In some embodiments the spacing between isotopic clusters in a convoluted spectrum can be irregular, for example, 1 Da between some adjacent isotopic cluster main peaks and two or more Daltons between other adjacent isotopic cluster main peaks. The spacing can be dependent on which isotopes are used to enrich the compounds (e.g., chlorine (34 Da) has isotopes of 35 Da and 37 Da). Whatever the nature of the isotopic cluster, the relative peak intensity and peak masses can be determined for each lot of compound. Accordingly, the actual characteristics of the isotopic clusters is not a limitation on the embodiments of this invention since it is possible to accommodate clusters of any shape, provided however that it is anticipated that the main peak of the isotopic cluster will not be the lowest mass component of the isotopic cluster.

FIG. 1 contains a color illustration of two overlapping isotopic clusters of two isotopically enriched compounds (e.g., a label, a fraction or part of a label or a labeled analyte). The isotopic cluster attributable to one compound is illustrated in red and the isotopic cluster attributable to a second compound is illustrated in blue. Because they have been isotopically enriched, the primary mass of the compound (represented by the main peak of the isotopic cluster) is greater than the mass of the non-enriched compound. However, because isotopic enrichment is not 100% effective, there are impurities of the compound that are of lesser degrees of enrichment and these will have a lower mass. Likewise, because of over-enrichment (undesired enrichment) and because of natural isotopic abundance, there can be impurities of greater mass. This is why a single compound can produce an isotopic cluster of the type illustrated wherein both at least one up-mass side peak and at least one down-mass side peak can be observed. It should therefore be apparent to the ordinary practitioner that an isotopic cluster of this type can therefore define a compound since the peaks associated with the isotopic cluster are associated with the presence of the compound. It will also be apparent that the intensity of the various peaks that define the isotopic cluster can vary from lot to lot of the enriched compound and can depend upon the state of enrichment of the compound resulting from the enrichment process as well as the natural abundance of isotopes. Accordingly, the relative intensity of the peaks that define the isotopic cluster can also be indicative or determinative of the lot or sample of the isotopically enriched compound used in an assay. For example, if the compound that produces an isotopic cluster is used to label an analyte, detection of the isotopic cluster, based upon its characteristic peak profile (i.e., ratio information), can be correlated with the presence and/or quantity of the analyte.

Some embodiments of the present invention include collecting reporter (i.e., a fragment ion of the compound used to label the analyte that produces the isotopic cluster) ions and daughter fragment ions of the labeled analyte (or a fragment thereof) in a single spectrum during a single energy scan (e.g., a mass spectrometer/mass spectrometer ("MS/MS") or a collision-induced dissociation ("CID") scan) in the analyzer. In some embodiments, this single scan can occur after an initial survey scan (e.g., a mass spectrometer ("MS") scan) whereby the initial scan can be used to identify the specific labeled analyte or labeled fragment of the analyte present in the sample being tested. Fragment ions of both the analyte and labeling reagent can be observed in the same scan where there is a balance (or similarity) in bond strengths between the bond linking the fragment generating the reporter ion to the analyte and the one or more bonds of the analyte that typically fragment to produce recognizable daughter fragment ion spectra. When a single scan is performed that generates both reporter ions (that generate the isotopic cluster) and daughter fragment ions, any quantitative analysis of the reporter ions can be simplified if the isotopic clusters exist in quiet zones.

In contrast, other systems require two energy scans (e.g., two MS/MS or CID scans) to quantitate the reporter and daughter fragment ions. One scan to analyze reporter ions that are useful for quantitation and a second scan to analyze daughter fragment ions of the labeled analyte. Two scans are required where the reporter ions break off (i.e., dissociate or fragment) from the analyte at a lower or higher energy level than is required to fragment the analyte into its recognizable daughter fragment ions. Moreover, if the reporter ions of other systems are not centered in a "quiet zone," quantitation of the reporter ions (i.e., the isotopic cluster) in a single scan would be difficult if the analyte produced daughter fragment ions that overlapped the isotopic cluster.

Specifically, after the initial MS survey scan, some current systems must first perform a low energy MS/MS or CID scan to generate the reporter ions and then increase the energy level to perform a separate high energy MS/MS or CID scan to fragment the analyte into its daughter fragment ions. However, this results in the reporter ions and daughter fragment ions being collected in two separate scan spectrums, which takes longer and creates additional information that must be stored and processed for each analyte identification and quantitative measurement.

With reference to FIG. 1 and the associated Table 1, in an exemplary convoluted spectrum comprising only two different isotopic clusters with main summary isotope peaks at 115 Da and 116 Da, the main summary isotope peaks (for this example a main summary isotope peak represents the intensity of the peak at a specified mass in the convoluted spectrum) can have summary peak intensities of 9.0 and 7.2, respectively. In addition, the two main summary isotope peaks can have down-mass side peaks at 114 Da and 115 Da with intensities of 0.5 and 0.3, respectively, and up-mass side peaks at 116 Da and 117 Da with intensities of 1.0 and 0.6, respectively. A normalized value for each main summary isotope peak can be obtained by removing (e.g., subtracting) the intensity contribution of the other isotopic cluster side peaks from and combining (e.g., adding) the side peak intensities associated with the main peak of each isotopic cluster. In this example, the following equation can be used to de-convolute the X Da isotopic cluster intensity ("$I_{Xmp}$") from the convoluted spectrum:

$$I_{Xmp}=SI_{Xmp}-I_{X-1\ umsp}-I_{X+1\ dmsp}+I_{Xdmsp}+I_{Xumsp},$$

where $SI_{Xmp}$ is the summary intensity of the main isotope peak at X Da; $I_{X-1\ umsp}$ is the intensity of the next lower (X−1 Da) up-mass side peak, which appears centered around X Da; $I_{X+1\ dmsp}$ is the intensity of the next higher (X+1 Da) down-mass side peak, which also appears centered around X Da; $I_{Xdmsp}$ is the intensity of the main isotope peak (X Da) down-mass side peak, which appears centered around X−1 Da; and $I_{Xumsp}$ is the intensity of the main peak (X Da) up-mass side peak, which appears centered around X+1 Da.

Therefore, in the simple two isotopic cluster example above, the quantitative main peak intensity of each peak can be determined as follows: $I_{115}$=9.0−0−0.3+0.5+1.0=10.2 and $I_{116}$=7.2−0−1.0+0.3+0.6−=7.1 (See Table 1). Thus, the normalized main peak intensity of the isotopic cluster at 115 Da is greater than the quantitative main peak intensity of the isotopic cluster at 116 Da.

The normalized peak intensities can be used in a variety of applications such as to perform a time course study. For example, if each of the isotopic tags (e.g., the 115 Da tag and the 116 Da tag) had been used to label the same analyte in each of two different samples that represent two different time points for an assay, (e.g., 115 Da at time 0 and 116 one hour later) a possible conclusion would be that the concentration of the analyte is reduced in the sample over time, since the relative intensity of the 115 Da tag is greater than the intensity of the 116 Da tag. Conversely, if the normalized peak intensity of the 115 Da tag had been found to be less than the quantitative main peak intensity of the 116 Da tag, then it might be possible to conclude that the concentration of the analyte would be increasing over time. In this way, it is possible to obtain qualitative and/or quantitative information by de-convoluting the convoluted spectrum.

In accordance with some embodiments of the present invention, each isotopically labeled compound can be separately combined with a different analyte and then the labeled analytes can be combined and analyzed to obtain the convoluted spectrum. In this embodiment, the final quantitative intensities obtained for each isotopic cluster can be used to determine the relative or absolute abundance of each of the different analytes in the combined sample.

In accordance with some embodiments of the present invention, in FIG. 1, the ratio information for the two isotope clusters can be obtained from independent experimentation to provide the relative abundance of each peak (e.g., down-mass side peak, main peak, and up-mass side peak) in an isotopic cluster. For example, in Table 1, it can be seen that for the 115 Da isotope cluster, it is known that the down-mass side peak contributes 4.9% of the total normalized intensity, the main peak contributes 85.3%, and the up-mass side peak contributes 9.8%. The ratio information can be provided separately from and/or associated with the convoluted spectrum information and can be used to de-convolute the convoluted spectrum to obtain the normalized peak intensity by determining the known peak intensity of each peak in the convoluted spectrum.

For example, in Table 1, the intensity of the peak at 114 Da of the convoluted spectrum is 0.5. That peak represents the down-mass side peak that is 4.9% of the isotopic cluster centered at 115 Da. Because it is known that the peak of the isotopic cluster (the main peak of the isotopic cluster) at 115 Da will be 85.3% of the isotopic cluster, it is possible to solve for the main peak intensity, x, using the ratio 0.5/0.049=x/0.853 to thereby determine the value of 8.7 (See Table 1). Similarly, because it is known that the peak of the isotopic cluster at 116 Da (the up-mass side peak of the isotopic cluster) will be 9.8% of the isotopic cluster, it is possible to solve for the up-mass side peak intensity, y, using the ratio 0.5/0.049=y/0.098 to thereby determine the value of 1.0 (See Table 1). Based upon these known peak intensities, it is possible to calculate the normalized peak intensity for the isotopic cluster centered at 115 Da as 0.5+8.7+1.0=10.2 (Table 1).

With all of the known peak intensities for the isotopic cluster centered at 115 Da, it is possible, for this example, to calculate the known peak intensity for all of the peaks of the isotopic cluster centered at 116 Da in either of two ways.

For example, it is possible to use the ratio information in the manner used above. Because the known peak intensity (0.6) of the up-mass side at 117 Da is 8.5% of the isotopic cluster, the known peak intensity of the peak at 116 Da (the main peak of the isotopic cluster) can be calculated by solving for the main peak intensity, x, using the ratio 0.6/0.085=x/0.873 to thereby determine the value of 6.2 (See Table 1). Similarly, because it is known that the peak at 115 Da will be 4.2% of the isotopic cluster (the down-mass side peak of the isotopic cluster) it is possible to solve for the down-mass side peak intensity, z, using the ratio 0.6/0.085=z/0.042 to thereby determine the value of 0.3 (See Table 1). Based upon these known peak intensities, it is possible to calculate the normalized peak intensity for the isotopic cluster centered at 116 Da as 0.3+6.2+0.6=7.1 (Table 1).

For the example provided, it is also possible to obtain information for the known peak intensity of the peaks of the isotopic cluster centered at 116 Da by analysis of the convoluted spectrum and the known peak intensities of the isotopic cluster centered at 115 Da. For example, since the intensity of the convoluted spectrum (9.0) at 115 Da is the summed intensity of the main peak of the isotopic cluster centered at 115 Da (calculated above to be 8.7), and the intensity contribution of the down-mass side peak of the isotopic cluster centered at 116 Da, the known peak intensity for the down-mass side peak of the isotopic cluster centered at 116 Da can simply be calculated as the difference of two known peak intensity values 9.0−8.7=0.3. Similarly, since the intensity of the convoluted spectrum (7.2) at 116 Da is the summed intensity of the main peak of the isotopic cluster centered at 116 Da, and the intensity contribution of the up-mass side peak of the isotopic cluster centered at 115 Da (calculated above to be 1.0), the known peak intensity for the main peak of the isotopic cluster centered at 116 Da can simply be calculated as the difference of two known values 7.2−1.0=6.2 (Table 1).

Regardless of how calculated, with the above information it is possible to calculate the normalized peak intensity for the isotopic cluster centered at 116 Da. The normalized peak intensity would be 0.3+6.2+0.6=7.1 (Table 1).

Accordingly, it is clear that given the convoluted spectrum and the relative intensity of the peaks that define the isotopic cluster, there are many different ways to calculate the normalized peak intensity for the isotopic cluster. The forgoing is exemplary and not intended to be limiting. Such calculations can be done with or without the aid of a machine (calculator or computer). Such calculation can be performed in any order that would produce the correct result.

In accordance with some embodiments of the present invention, an isotopic peak can be defined by the formula:

$$I(m)=I_o\exp(-(m-\mu)^2/\sigma^2),$$

where m is mass, I is intensity at a given mass, μ is a peak position parameter (centroid), and σ is a peak width parameter. The peak width (σ) can be measured as the width between a peak's sides at one-half the height of the peak. Actual measurement of peak width can be accomplished by empirically measuring across the range at one-half the height of the peak or by iteratively calculating by fitting the convoluted spectrum data to a specific curve type, for example, a Gaussian curve.

In accordance with some embodiments of the present invention, an isotopic cluster is a sum of isotopic peaks and can be defined by the formula:

$$I(m)=\sum_{i=0}^{n} I_i\exp(-(m-\mu_i)^2/\sigma_i^2),$$

where n is a number of isotopic peaks in the convoluted spectrum relevant to the calculation of a de-convoluted spectrum. In general, n can depend on the mass range, for example, for a mass range between 100 to 1700 Da, n can range from 2 to 6. Some other embodiments can involve different mass ranges such that n can range from 2 to more than 6.

In accordance with some embodiments of the present invention, a convoluted spectrum can be defined as a sum of isotopic clusters with linear dependence on concentration, which can be defined by the formula:

$$I(m)=\sum_{j=0}^{t} c_j\sum_{i=0}^{n} I_{ji}\exp(-(m-\mu_{ji})^2/\sigma_{ji}^2),$$

where I is a number of convoluted components and c is a normalized concentration of an individual component. The normalized concentration, c, can be determined for every j using a known intensity, $I_{ji}$, at each given mass in the isotopic cluster. The intensities can be known either from theoretical calculations based on a known chemical formula or from a prior measurement of an isotopic abundance of the compound associated with the isotopic cluster for each individual components. For example, the composition of the isotopic cluster of each compound can be determined by individual mass analysis of each compound or a sample thereof. Once determined, this information can be provided simultaneously with the convoluted spectrum data or be provided before or after the convoluted spectrum. In addition, the known intensity information can be permanently and/or temporarily stored for use in embodiments of the present invention.

In general, in accordance with an embodiment of the present invention, the computational procedure can include calculating all concentration parameters when a merit function, F, is minimal, for example:

$$F(I_{experiment}-I(m))\Rightarrow \min,$$

where some possible merit functions can include, but are not limited to:

$$x^2=(I_{experiment}-I(m)^2)\Rightarrow \min,\quad \text{and}$$

$$|x|=\Sigma|I_{experiment}-I(m)|\Rightarrow \min$$

Accordingly, this is still another way to calculate normalized peak intensity data for the isotopic cluster and thereby deconvolute a convoluted spectrum.

In accordance with some other embodiments of the present invention, quantitation of the normalized intensities of the peaks can be calculated using linear algebra, for example, AX=B, where A is a matrix of theoretical normalized intensities of each isotope tag; B is a vector of observed output peak intensities in the spectrum; and X is a vector of the relative quantitation amounts. For example, A, B and X can be represented by the following:

MATRIX A

| Mass | w | x | y | z |
|---|---|---|---|---|
| 113 | 0.04 | 0.00 | 0.00 | 0.00 |
| 114 | 0.90 | 0.04 | 0.00 | 0.00 |
| 115 | 0.06 | 0.90 | 0.04 | 0.00 |
| 116 | 0.00 | 0.06 | 0.90 | 0.04 |
| 117 | 0.00 | 0.00 | 0.06 | 0.90 |
| 118 | 0.00 | 0.00 | 0.00 | 0.06 |

VECTOR B

| |
|---|
| Peak Area at 113 |
| Peak Area at 114 |
| Peak Area at 115 |
| Peak Area at 116 |
| Peak Area at 117 |
| Peak Area at 118 |

VECTOR X

| |
|---|
| w |
| x |
| y |
| z |

As seen in Matrix A, the values of w, x, y and z for each mass tag should add up to 1.0 (i.e., 100%) when at least 3 of the values of w, x, y and z are greater than 0.0. The values of w, x, y and z can be measured or theoretical ratios of each of the different labeling reagents and, generally, can be derived from measuring the intensities of the pure reagents. Although Matrix A is shown as a 6×4 matrix where there are more peaks (e.g., from 113 Da to 118 Da) than reagents (e.g., w, x, y and z), any size matrix can be used. For example, a square matrix, such as a 5×5 matrix, as well as a matrix with more columns than rows, such as a 7×9 matrix can also be used.

In accordance with the current embodiment of the present invention, since A is not a square matrix, the following solution to solve AX=B can be derived:

1. Transpose(A)AX=Transpose(A)B

2. Inverse(Transpose(A)A)(Transpose(A)A)X=Inverse (Transpose(A)A)Trans-pose(A)B

3. X=Inverse(Transpose(A)A)Transpose(A)B Any standard matrix library, for example, any of the appropriate standard matrix libraries found in the *Numerical Recipes* books and/or software from Cambridge University Press, can be used to perform the matrix multiplication, transpose and inverse code calculations defined in the above equations. In general, these calculations can be performed simultaneously and can be preformed using a singular-value decomposition (SVD) algorithm, which can provide the most robust solution.

Accordingly, this is still another way to calculate normalized peak intensity data for the isotopic cluster. In accordance with this invention, any suitable method can be used to generate normalized peak intensity data for the isotopic cluster. Thus, the method used to generate normalized peak intensity data is not a limitation. Moreover, in some embodiments it may be possible to apply two or more different methods to that analysis of peak intensities of the same isotopic cluster or to the analysis of peak intensities of different isotopic clusters.

Figure 2:
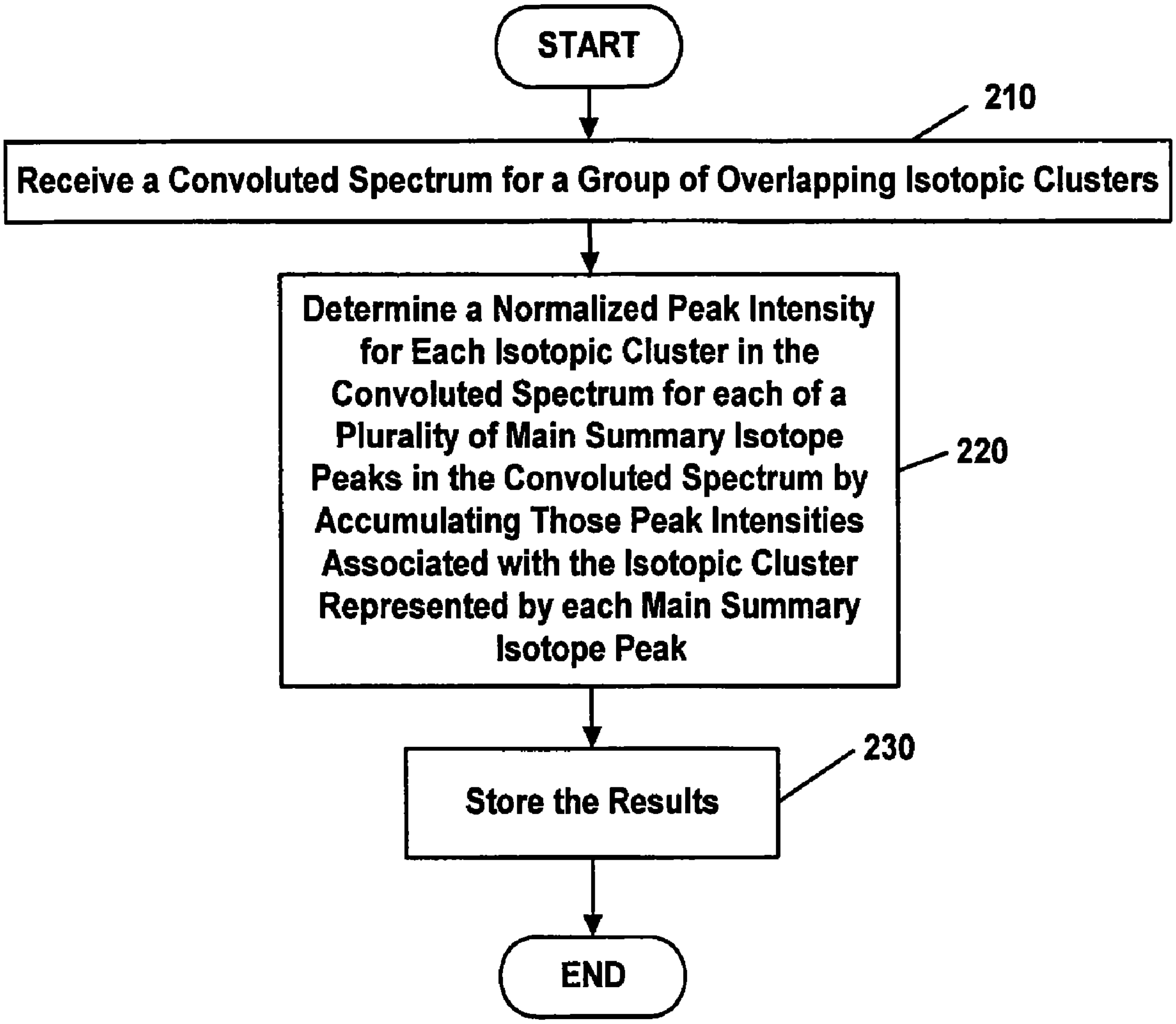
FIG. 2 is a top-level flow diagram of a method embodiment for de-convoluting intensity information in a convoluted spectrum.

FIG. 2 is a flow diagram of a method embodiment for de-convoluting intensity information in a convoluted spectrum. According to FIG. 2, a convoluted spectrum for a group of overlapping isotopic clusters can be received (210). A normalized peak intensity for a main summary isotope peak in the convoluted spectrum can be determined (220) for each of a plurality of main summary isotope peaks in the convoluted spectrum by accumulating those peak intensities associated with the isotopic cluster represented by each main summary isotope peak.

In FIG. 2, in some embodiments of the present invention, the accumulating can be accomplished by subtracting known peak intensities not associated with the isotopic cluster represented by the main summary isotope peak and adding known peak intensities of different masses associated with the isotopic cluster represented by the main summary isotope peak to the main summary isotope peak intensity. For example, a peak intensity associated with a main summary isotope peak of an isotopic cluster can be selected and known peak intensities of side peaks associated with other isotopic clusters can be subtracted from the selected main summary isotope peak intensity to obtain a temporary peak intensity. A known intensity of at least one down-mass side peak and a known intensity of at least one up-mass side peak of the selected main summary isotope peak can be added to the temporary peak intensity to thereby obtain the normalized peak intensity for the isotopic cluster.

The above order of the peak intensity subtraction and peak intensity addition is merely illustrative of the present embodiment and should not be taken to indicate an explicit order, since the correct result would be obtained by first adding the appropriate peak intensities to obtain a temporary peak intensity and then subtracting the appropriate peak intensities from the temporary peak intensity. Regardless of the order of processing, the results can be stored (230) for future output and/or can be immediately output and the method can terminate.

Figure 3:
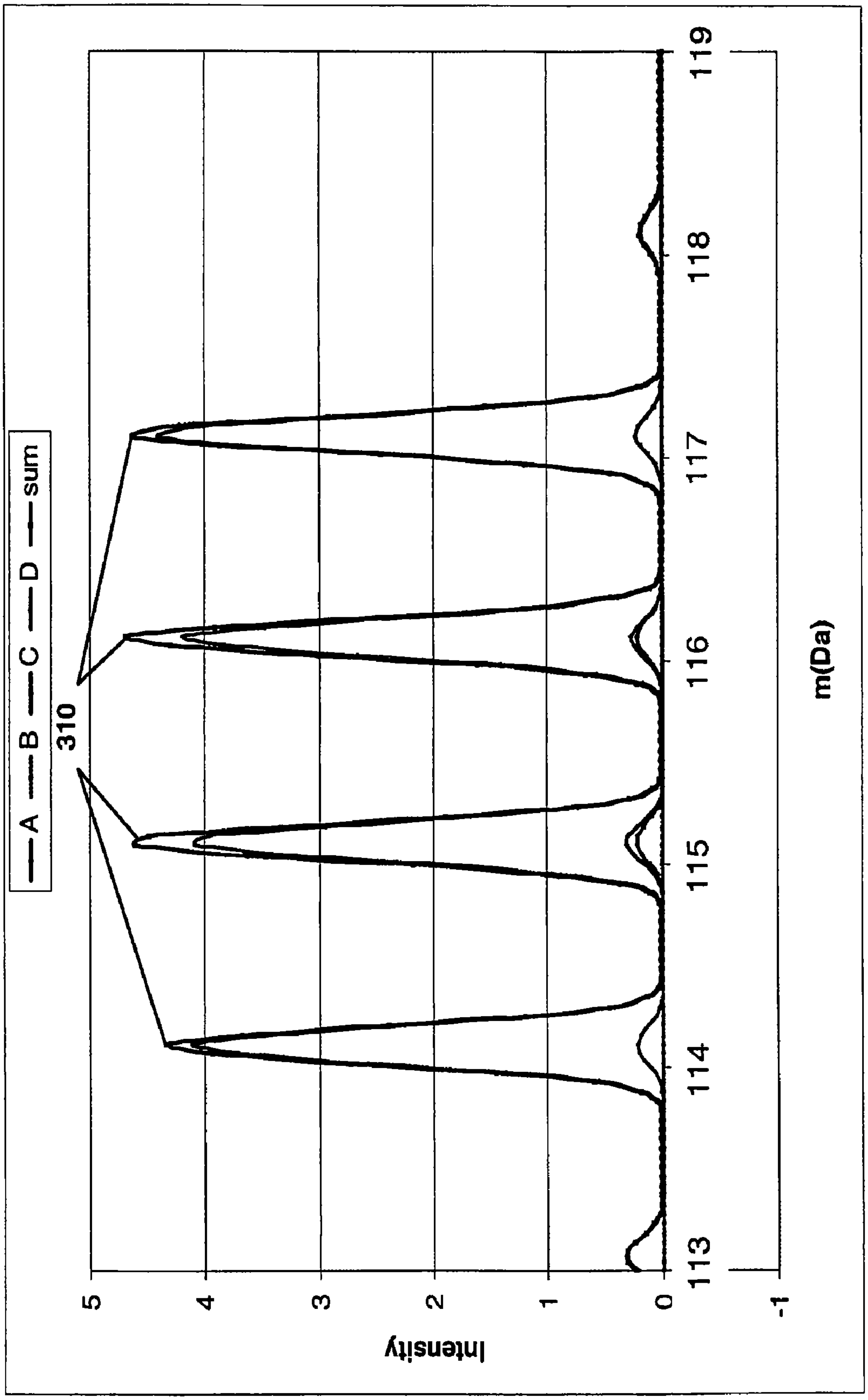
FIG. 3 is a color illustration of four overlapping isotopic clusters and a simulated convoluted spectrum for the group of four overlapping isotopic clusters.
Figure 4A:
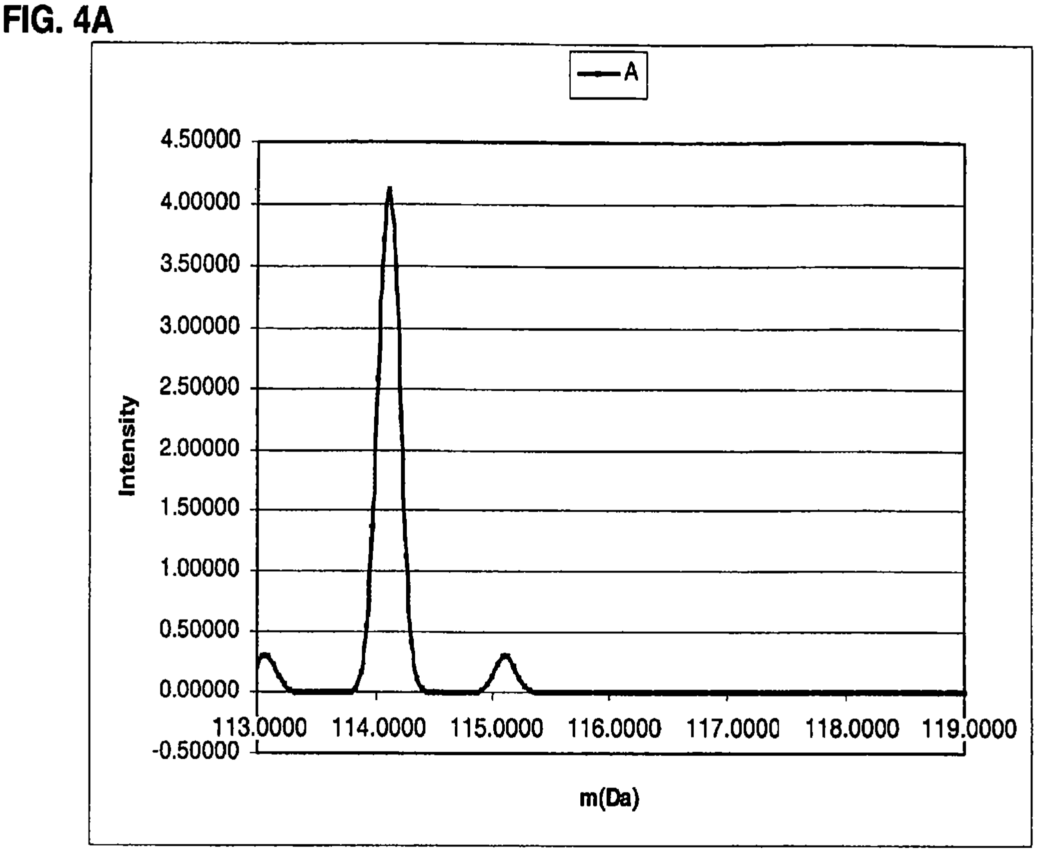
FIGS. 4A-4D are color examples of the four individual isotopic clusters that can be wave summed to form the convoluted spectrum of FIG. 3.
Figure 4B:
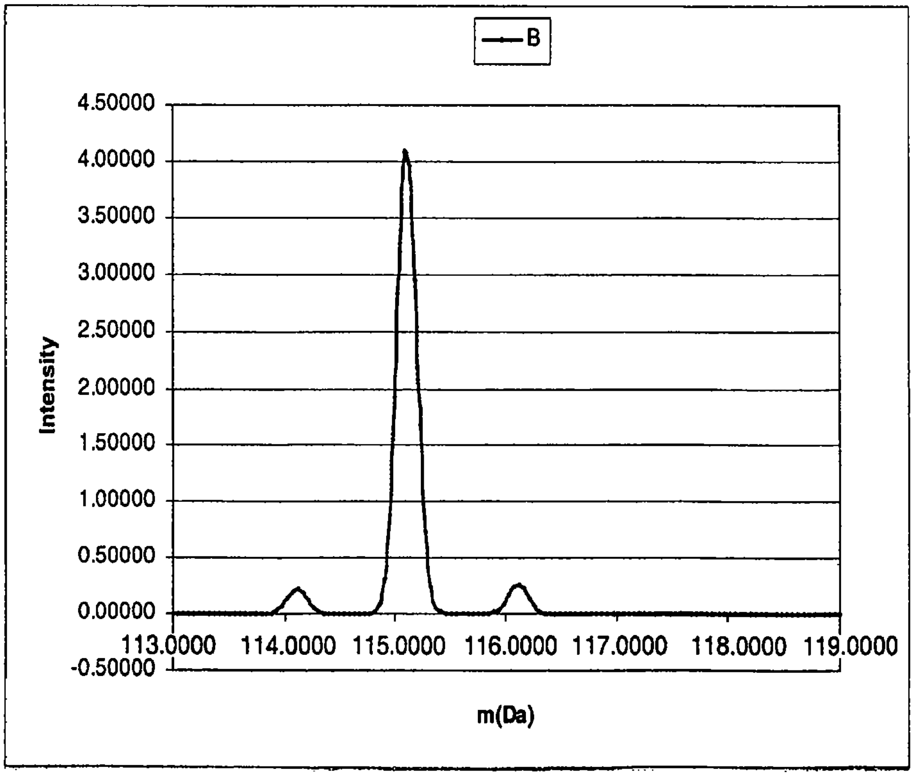
Figure 4C:
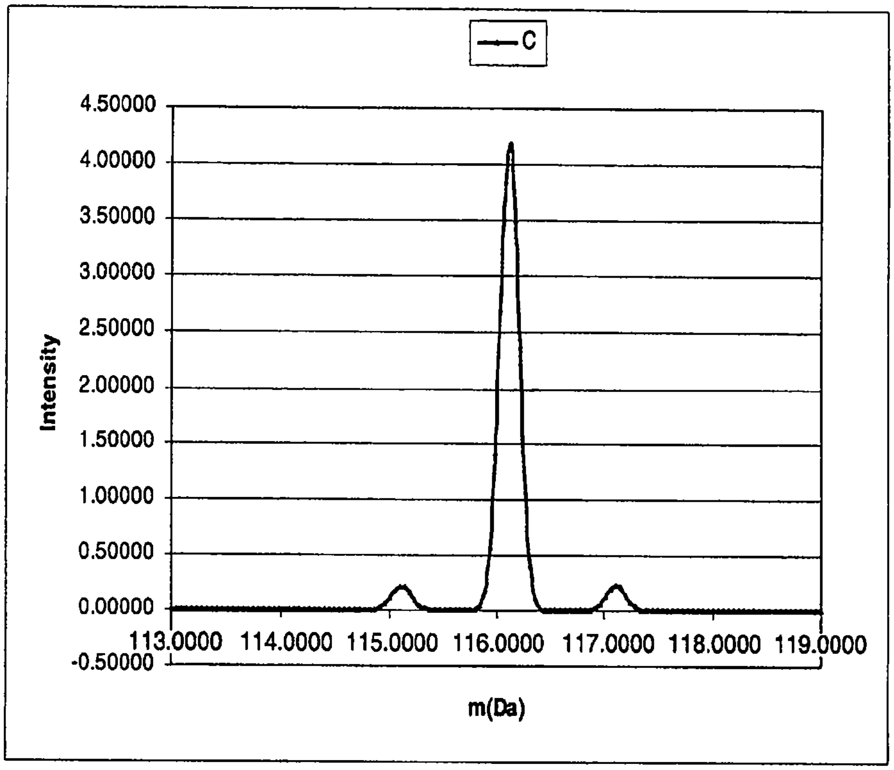
Figure 4D:
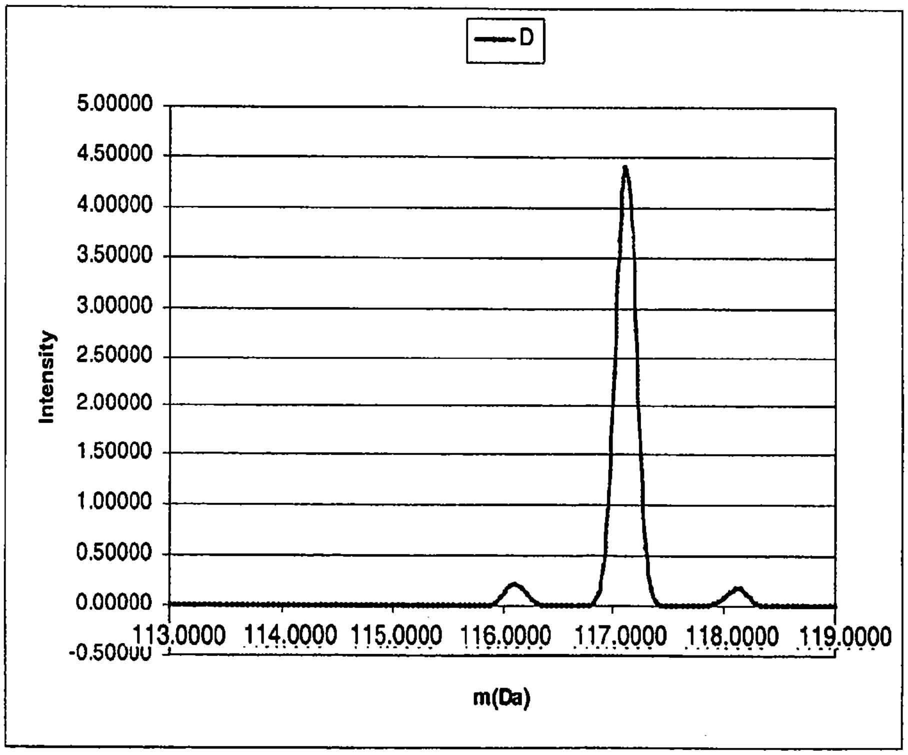

FIG. 3 is an illustration of four overlapping isotopic clusters displayed with a simulated convoluted spectrum that is the sum of the peak intensities for the group of four overlapping isotopic clusters. The Figure illustrates a more complex example of a convoluted spectrum as compared with FIG. 1. The convoluted spectrum can be de-convoluted using embodiments of the present invention. A convoluted spectrum 310 can be seen to include four separate main summary isotopic peaks A, B, C, D, each having an approximate mass of 114, 115, 116 and 117 Da, respectively. The convoluted spectrum 310 is created by summation of all of the individual isotopic clusters for all four isotopically enriched compounds. Although convoluted spectrum 310 is shown to include four separate summary isotope peaks A, B, C and D, a convoluted spectrum curve can comprise two or more separate isotopic peaks.

FIGS. 4A through 4D illustrate isotopic clusters of isotopically enriched compounds. FIGS. 4A through 4D are the individual isotopic clusters used to create the convoluted spectrum illustrated in FIG. 3. In the isotopic cluster in FIG. 4A, a main peak can be seen at 114 Da. A down-mass side peak can be seen at 113 Da and an up-mass side peak can be seen at 115 Da. In the isotopic cluster in FIG. 4B, a main peak can be seen at 115 Da. A down-mass side peak can be seen at 114 Da and an up-mass side peak can be seen at 116 Da. In the isotopic cluster in FIG. 4C, a main peak can be seen at 116 Da. A down-mass side peak can be seen at 115 Da and an up-mass side peak can be seen at 117 Da. In the isotopic cluster in FIG. 4D, a main peak can be seen at 117 Da. A down-mass side peak can be seen at 116 Da and an up-mass side peak can be seen at 118 Da. In all of the isotopic clusters illustrated in FIGS. 4A through 4D, there is a single up-mass side peak and a single down-mass side peak. However, as previously stated in some embodiments it is worthwhile to consider the contributions of two or more up-mass side peaks and/or two or more down-mass side peaks.

Figure 5:
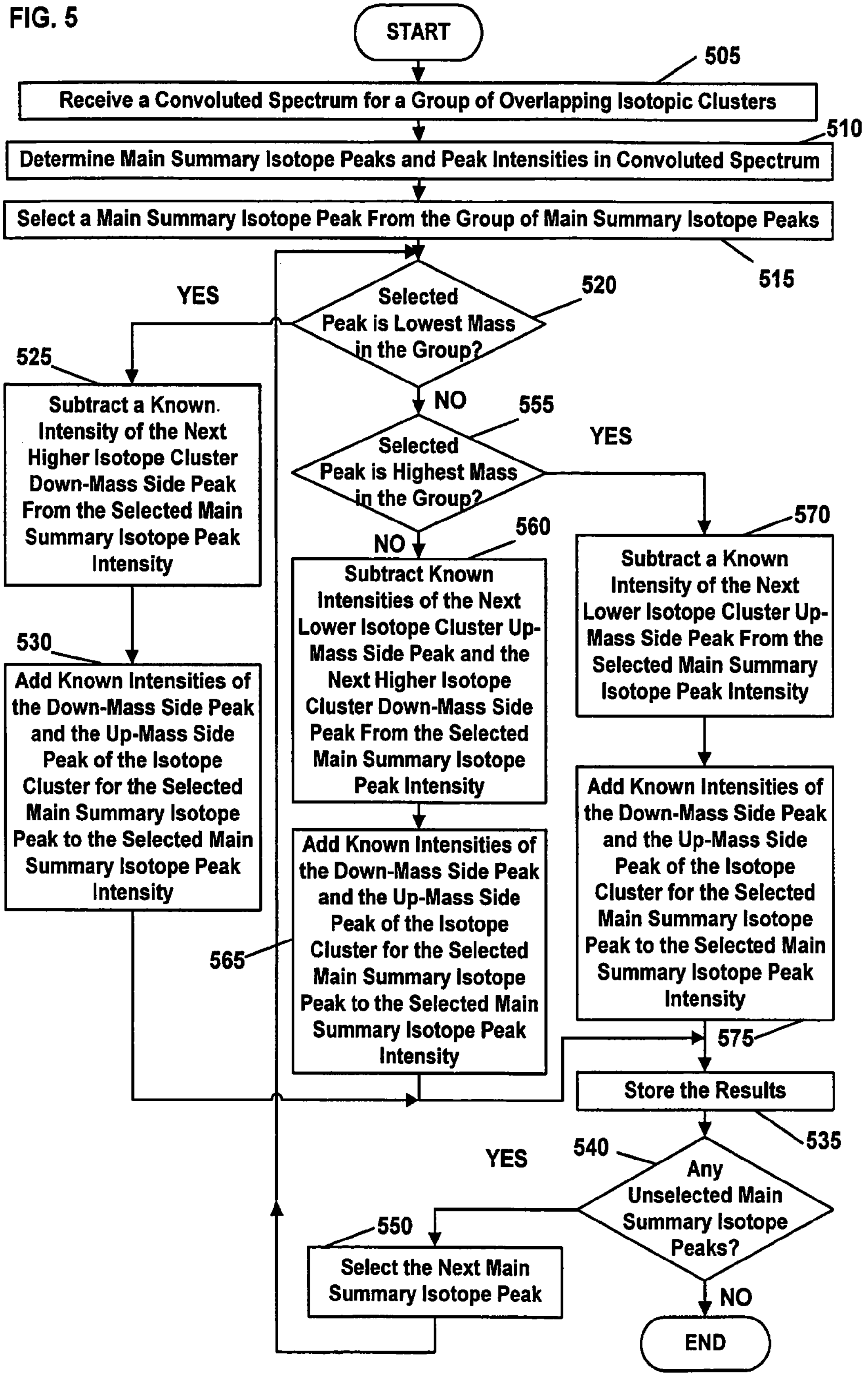
FIG. 5 is a flow diagram of a method embodiment for de-convoluting intensity information in a convoluted spectrum.

FIG. 5 is a flow diagram of a method embodiment for de-convoluting intensity information in a convoluted spectrum. The method can be used, for example, to de-convolute the convoluted spectrum of overlapping isotopic clusters illustrated in FIG. 1 or 3. According to FIG. 5, a convoluted spectrum for a group of overlapping isotopic clusters can be received (505) and main summary isotope peaks and peak intensities of the summary isotope peaks in the convoluted spectrum can be determined (510). One main summary isotope peak from the group of overlapping isotopic clusters can be selected (515). Whether the selected peak has the lowest isotopic mass of the main summary isotope peaks in the group can be determined (520). For example, in a group of four overlapping isotopic clusters with the main summary isotope peaks having masses of 114, 115, 116 and 117 Da, the lowest mass would be 114 Da (e.g., FIG. 3). If the selected peak has the lowest mass (e.g., 114 Da), a known intensity of the next-higher isotope cluster (main peak 115 Da) down-mass side peak (located at 115 Da) can be subtracted (525) from the selected main summary isotope peak intensity to obtain a temporary peak intensity. A known intensity of a down-mass side peak (located at 113 Da) and a known intensity of an up-mass side peak (located at 115 Da) of the selected main summary isotope peak can be added (530) to the temporary peak intensity to thereby obtain the normalized peak intensity for the lowest mass isotope (or isotopic cluster) of the convoluted spectrum. The above order of the peak intensity subtraction (525) and peak intensity addition (530) is merely illustrative of the present embodiment and should not be taken to indicate an explicit order, since the correct result would be obtained by first adding (530) the appropriate peak intensities and then subtracting (525) the appropriate peak intensities from the main summary isotope peak intensities. Regardless of the order of processing, the results can be stored (535) for future output and/or immediately output.

Whether unselected main summary isotope peaks remain in the group of overlapping isotopic clusters can be determined (540) and, if none remain, the method can terminate. If it is determined (540) that additional unselected main summary isotope peaks remain, a next main summary isotope peak can be selected (550) and the method can return to determine (520) whether the selected main summary isotope peak has the lowest isotopic mass of the main summary isotope peaks in the group. The above elements, in general, should only need to be performed once, since there can only be a single lowest mass main summary isotope peak in the group.

In FIG. 5, if the selected main summary isotope peak is not determined (520) to have the lowest mass of the main summary isotope peaks in the group, whether the selected main summary isotope peak has the highest mass of the main summary isotope peaks in the group can be determined (555). If the selected main summary isotope peak does not have the highest mass, a known intensity of the next-higher isotopic cluster down-mass side peak and a known intensity of a next-lower isotopic cluster up-mass side peak can be subtracted (560) from the selected main summary isotope peak intensity to obtain a temporary peak intensity. A known intensity of a down-mass side peak and a known intensity of an up-mass side peak of the selected main summary isotope peak can be added (565) to the temporary peak intensity to thereby obtain the normalized peak intensity for this isotopic cluster. As was the case for the lowest mass main summary isotope peak, the above order of the subtracting (560) peak intensity and adding peak intensity (565) intensity is merely illustrative of the present embodiment and should not be taken to indicate an explicit order, since the correct result would be obtained by first adding (565) the appropriate peak intensities and then subtracting (560) the appropriate peak intensities of the main summary isotope peaks. Regardless of the order of processing, the results can be stored (535) for future output and/or immediately output.

According to the method in FIG. 5, whether unselected main summary isotope peaks remain in the group can be determined (540) and, if none remain, the method can terminate. If it is determined (540) that additional unselected main summary isotope peaks remain, a next main summary isotope peak can be selected (550) and the method can return to determine (520) whether the selected main summary isotope peak has the lowest mass in the group. If the selected main summary isotope peak is determined (520) to have neither the lowest mass (520) nor the highest mass (555) of any of the main summary isotope peaks, the method can continue as described above. The above elements, in general, can be performed one or more times depending on the number of intermediate isotopic clusters. For example, for a group of three isotopic clusters there will be one intermediate isotopic cluster, for four isotopic clusters there will be two intermediate isotopic clusters, etc. In other words, the number of intermediate isotopic clusters will be two less than the total number of isotopic clusters in the group.

According to FIG. 5, if the selected main summary isotope peak is not determined (520) to have the lowest mass in the group, whether the selected main summary isotope peak has the highest mass can be determined (555). If the selected main summary isotope peak does have the highest mass, a known intensity of a next-lower isotope cluster up-mass side peak can be subtracted (570) from the selected main summary isotope peak intensity to obtain a temporary peak intensity. A known intensity of a down-mass side peak and a known intensity of an up-mass side peak of the selected main summary isotope peak can be added (575) to the temporary peak intensity to thereby obtain the normalized peak intensity for the highest mass isotopic cluster of the convoluted spectrum. As was the case for the lowest and intermediate mass main summary isotope peaks, the above order of the peak intensity subtraction (570) and peak intensity addition (575) is merely illustrative of the present embodiment and should not be taken to indicate an explicit order, since the correct result would be obtained by first adding (575) the appropriate peak intensities and then subtracting (570) the appropriate peak intensities. Regardless of the order of processing, the results can be stored (535) for future output and/or immediately output.

According to the method in FIG. 5, whether unselected main summary isotope peaks remain in the group can be determined (540) and, if none remain, the method can terminate. If it is determined (540) that additional unselected main summary isotope peaks remain, a next main summary isotope peak can be selected (550) and the method can return to determine (520) whether the selected main summary isotope peak has the lowest mass and continue processing as described.

The above description of the method illustrated in FIG. 5 should not be taken to indicate that the above order is required to practice the invention, but is instead merely illustrative of one possible order. As illustrated and described above, the order of execution can be from the lowest mass main summary isotope peak to the highest mass main summary isotope peak, from the highest mass main summary isotope peak to the lowest mass main summary isotope peak, or in any random order of the main summary isotope peaks.

Figure 6:
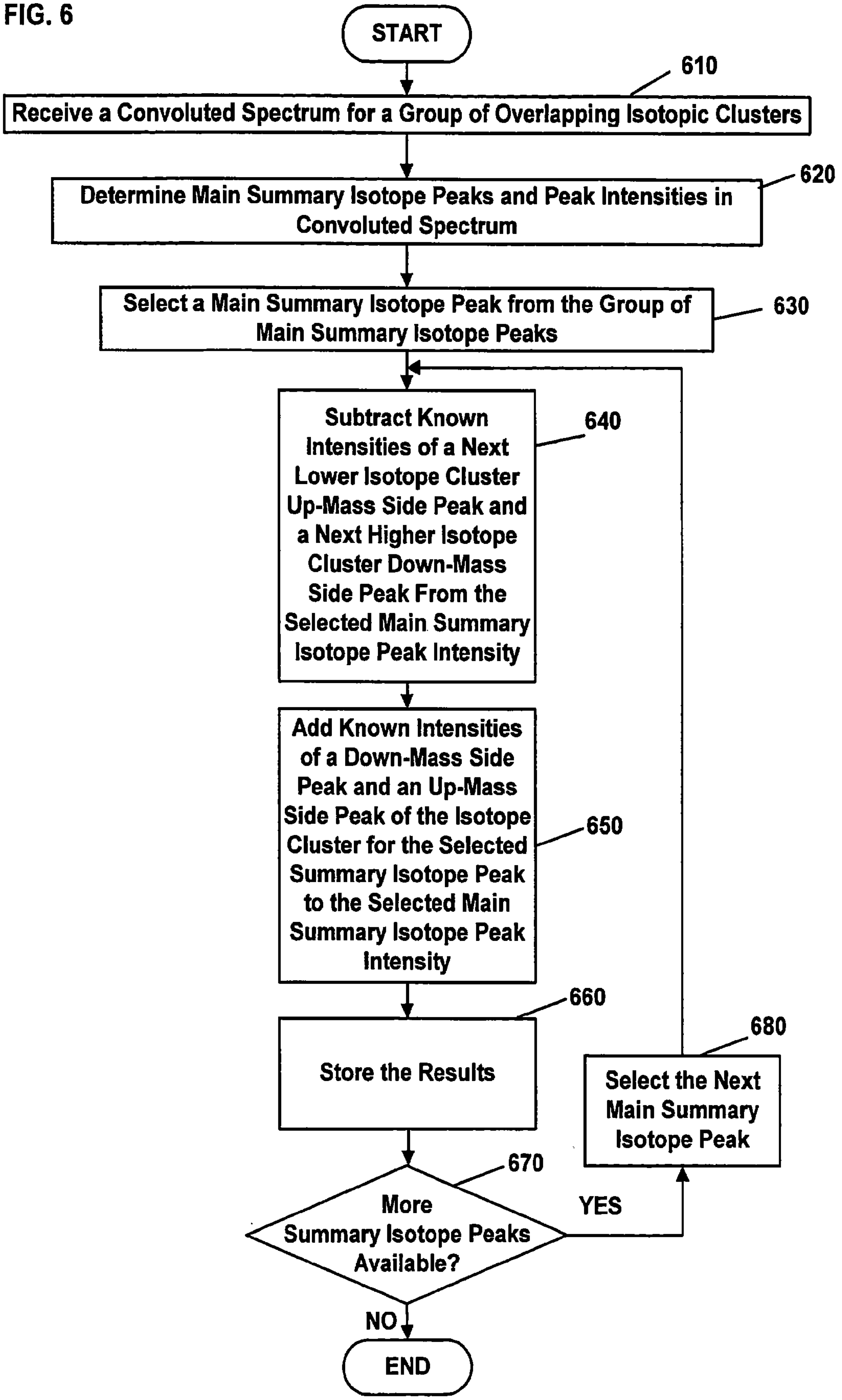
FIG. 6 is a flow diagram of another method embodiment for de-convoluting intensity information in a convoluted spectrum.

FIG. 6 is a flow diagram of another method embodiment for de-convoluting intensity information in a convoluted spectrum. The method can be used, for example, to de-convolute the convoluted spectrum of overlapping isotopic clusters illustrated in FIG. 1 or 3. In FIG. 6, a convoluted spectrum for a group of overlapping isotopic clusters can be received (610). Main summary isotope peaks and peak intensities of the summary isotope peaks in the convoluted spectrum can be determined (620) and one main summary isotope peak from the group of main summary isotope peaks can be selected (630).

Unlike FIG. 5, in the embodiment illustrated by FIG. 6, determining whether the selected main summary isotope peak has the lowest, highest or an intermediate mass is not necessary. A known intensity of the next-higher isotope cluster down-mass side peak and a known intensity of a next-lower isotope cluster up-mass side peak can be subtracted (640) from the selected main summary isotope peak to obtain a temporary peak intensity. A known intensity of a down-mass side peak and a known intensity of an up-mass side peak of the selected main summary isotope peak can be added (650) to the temporary peak intensity to thereby obtain the normalized peak intensity for the highest mass isotopic cluster of the convoluted spectrum. As was the case in the discussion of FIG. 5, in FIG. 6, the above order of the peak intensity subtraction (640) and peak intensity addition (650) is merely illustrative of the present embodiment and should not be taken to indicate an explicit order, since the correct result would be obtained by first adding (650) the appropriate peak intensities and then subtracting (640) the appropriate peak intensities. Regardless of the order of processing, the results can be stored (660) for future output and/or immediately output.

In FIG. 6, whether unselected main summary isotope peaks remain in the group can be determined (670) and, if none remain, the method can terminate. If it is determined (670) that additional unselected main summary isotope peaks remain, a next main summary isotope peak can be selected (680) and the method can return to subtract (640) and to add (650) the known peak intensities from the newly selected (680) main summary isotope peak.

Figure 7:
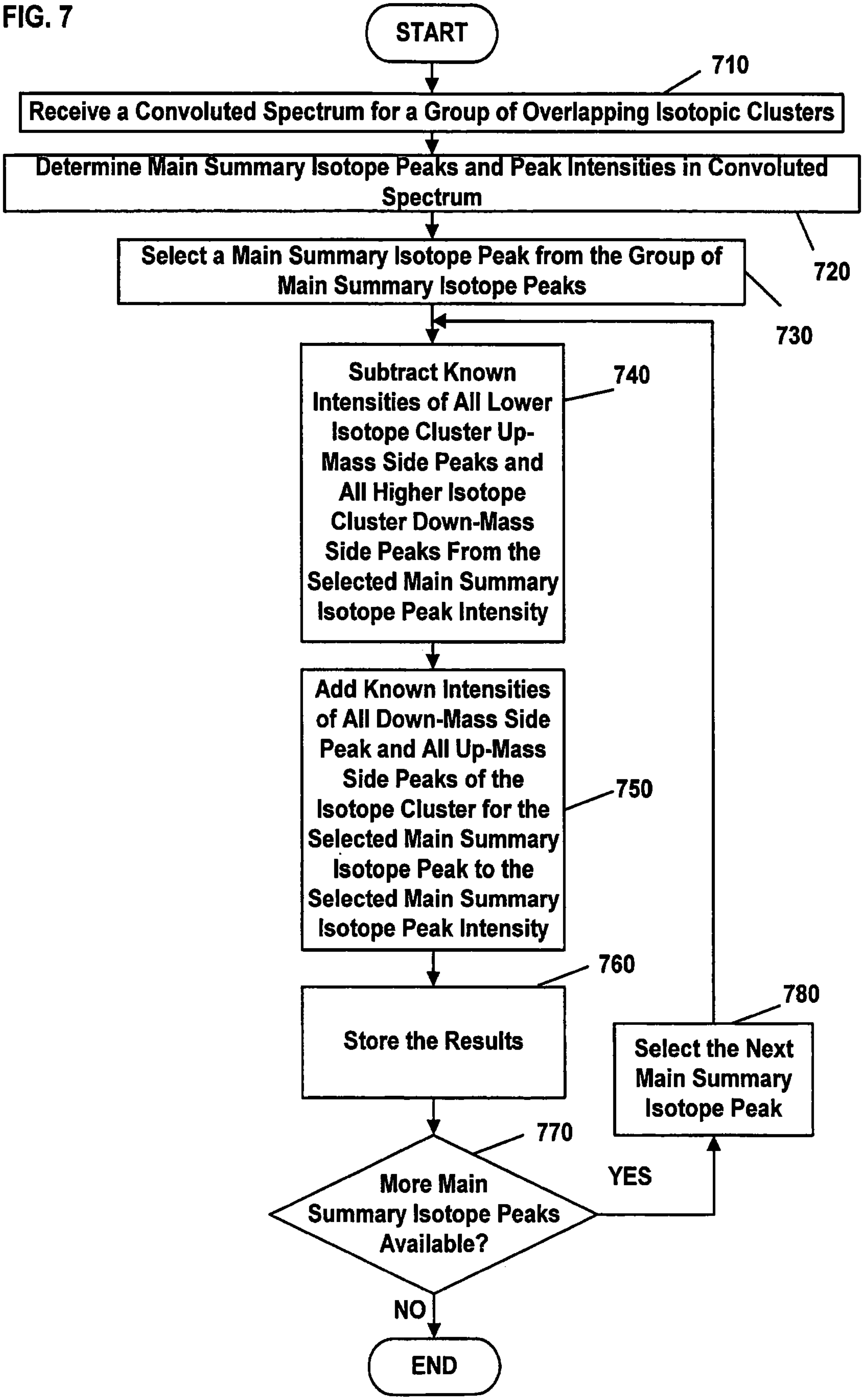
FIG. 7 is a flow diagram of still another method embodiment for de-convoluting intensity information in a convoluted spectrum.

FIG. 7 is a flow diagram of still another method embodiment for de-convoluting intensity information in a convoluted spectrum. The method can be used, for example, to de-convolute the convoluted spectrum of overlapping isotopic clusters illustrated in FIG. 1 or 3. In FIG. 7, a convoluted spectrum for a group of overlapping isotopic clusters can be received (710). Main summary isotope peaks and peak intensities of the summary isotope peaks in the convoluted spectrum can be determined (720) and one main summary isotope peak from the group can be selected (730). Unlike FIG. 5, in the embodiment illustrated in FIG. 7, determining whether the selected main summary isotope peak has the lowest, highest or an intermediate mass is not necessary. A known intensity of all higher isotope cluster down-mass side peaks and a known intensity of all lower isotope cluster up-mass side peaks can be subtracted (740) from the selected main summary isotope peak intensity to obtain a temporary peak intensity for the selected main summary isotope peak. A known intensity of all down-mass side peaks and a known intensity of all up-mass side peaks of the selected main summary isotope peak can be added (750) to the temporary peak intensity to thereby obtain a normalized peak intensity for the isotopic cluster associated with the selected main summary isotope peak.

As was the case in the discussion of FIG. 5, in FIG. 7, the above order of the peak intensity subtraction (740) and peak intensity addition (750) is merely illustrative of the present embodiment and should not be taken to indicate an explicit order, since the correct result can also be obtained by first adding (750) the appropriate peak intensities and then subtracting (740) the appropriate peak intensities. Regardless of the order of processing, the results can be stored (760) for future output and/or immediately output.

In FIG. 7, whether unselected main summary isotope peaks remain in the group can be determined (770) and, if none remain, the method can terminate. If it is determined (770) that additional unselected main summary isotope peaks remain, a next main summary isotope peak can be selected (780) and the method can return to subtract (740) and add (750) the known peak intensities from the newly selected (780) main summary isotope peak. This continues until all main summary isotope peaks have been processed, at which time the method may terminate.

Figure 8:
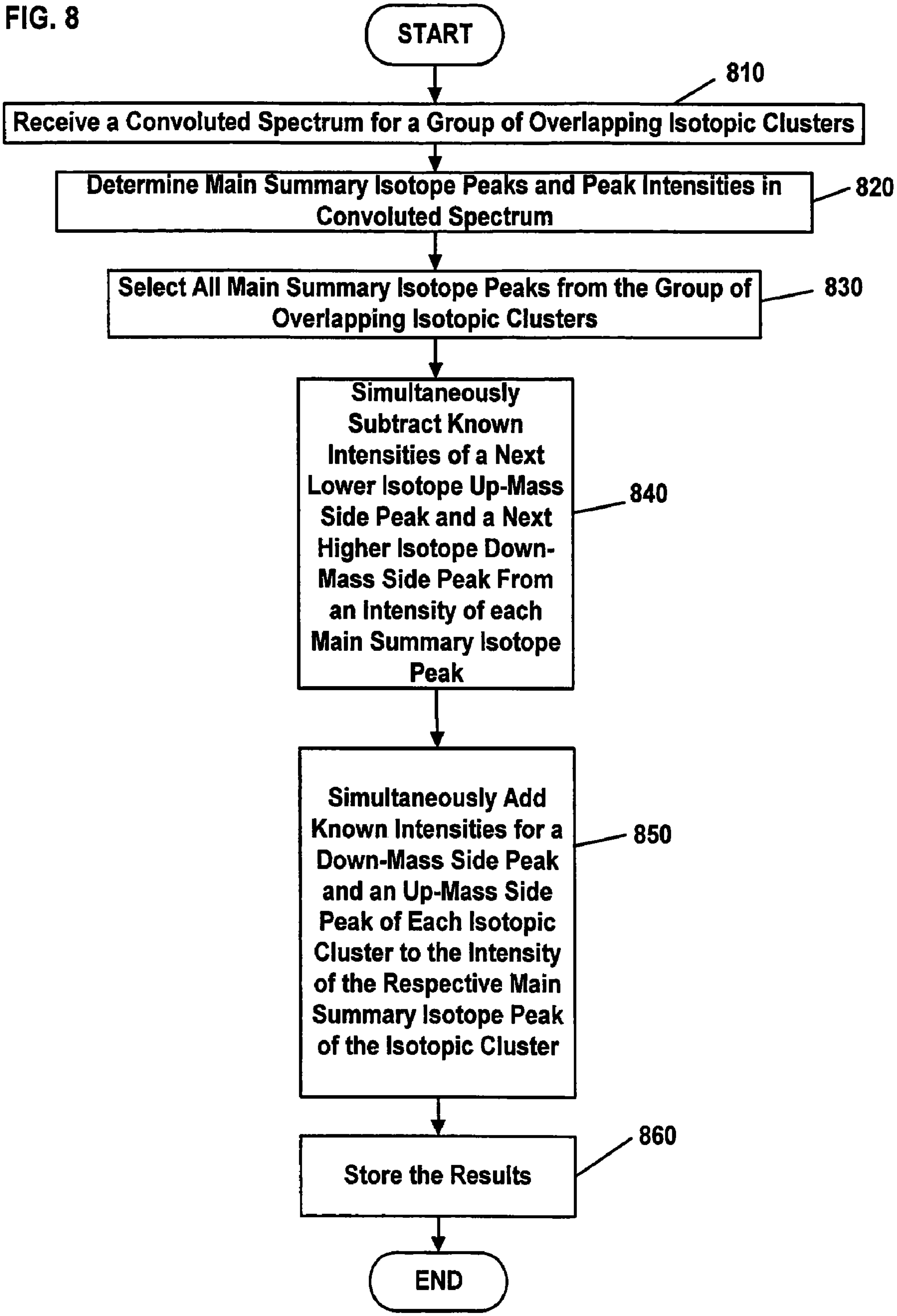
FIG. 8 is a flow diagram of a method embodiment for simultaneously de-convoluting intensity information in a convoluted spectrum.

FIG. 8 is a flow diagram of yet another method embodiment for de-convoluting intensity information in a convoluted spectrum wherein some of the steps of the method are performed simultaneously. The method can be used, for example, to de-convolute the convoluted spectrum of overlapping isotopic clusters illustrated in FIG. 1 or 3. In FIG. 8, a convoluted spectrum for a group of overlapping isotopic clusters can be received (810). Main summary isotope peaks and peak intensities of the summary isotope peaks in the convoluted spectrum can be determined (820) and all of the main summary isotope peaks from the group can be selected (830). Similar to FIG. 7, in the embodiment illustrated in FIG. 8, determining whether the selected main summary isotope peak has the lowest, highest or an intermediate mass is not necessary. A known intensity of the next-higher isotope cluster down-mass side peak and a known intensity of a next-lower isotope cluster up-mass side peak can be subtracted (840) simultaneously from each of the selected main summary isotope peak intensities to obtain temporary peak intensities for each main summary isotope peak. A known intensity of a down-mass side peak and a known intensity of an up-mass side peak for each of the selected main summary isotope peaks can be added (850) simultaneously to each of the respective temporary peak intensities to thereby obtain a normalized peak intensity for each isotopic cluster associated with each of the main summary isotope peaks of the convoluted spectrum.

As was the case with FIG. 5, in FIG. 8, the above order of the simultaneous peak intensity subtraction (840) and peak intensity addition (850) is merely illustrative of the present embodiment and should not be taken to indicate an explicit order, since the correct result would be obtained by first simultaneously adding (850) the appropriate respective peak intensities and then simultaneously subtracting (740) the appropriate respective peak intensities from the respective appropriate main summary isotope peaks. In some embodiments, all additions and all subtractions are simultaneously processed (e.g., when wave function analysis is performed.) Regardless of the order of processing, the results can be stored (860) for future output and/or can be immediately output and the method can terminate. In accordance with some embodiments of the present invention, a matrix structure, for example, a 40 by 40 matrix, can be used to perform the subtractions (840) and additions (850) and to store (880) the results.

Figure 9:
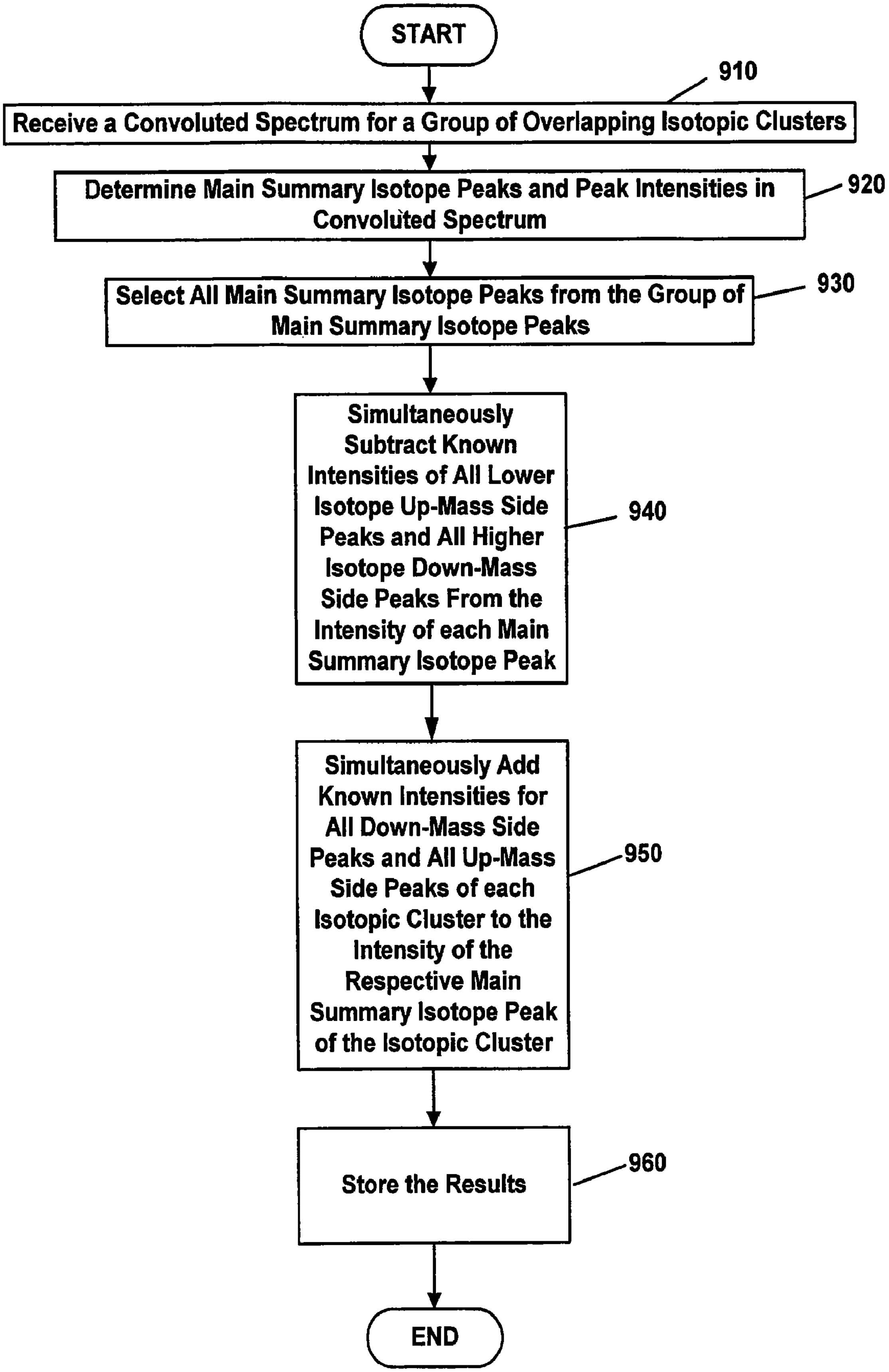
FIG. 9 is a flow diagram of still another method embodiment for simultaneously de-convoluting intensity information in a convoluted spectrum.

FIG. 9 is a flow diagram of still another method embodiment for simultaneously de-convoluting intensity information in a convoluted spectrum. The method can be used, for example, to de-convolute the convoluted spectrum of overlapping isotopic clusters illustrated in FIG. 1 or 3. In FIG. 9, a convoluted spectrum for a group of overlapping isotopic clusters can be received (910). Main summary isotope peaks and intensities of the summary isotope peaks in the convoluted spectrum can be determined (920) and all of the main summary isotope peaks from the group can be selected (930). Similar to FIG. 7, in the embodiment illustrated by FIG. 9, determining whether the selected summary isotope peak has the lowest, highest or an intermediate mass is not necessary. Known intensities of all higher isotope cluster down-mass side peaks and known intensities of all lower isotope cluster up-mass side peaks can be subtracted (940) simultaneously from each of the selected main summary isotope peak intensities to obtain a temporary peak intensity for each main summary isotope peak. A known intensity of all down-mass side peaks and a known intensity of all up-mass side peaks of each selected main summary isotope peak can be added (950) simultaneously to the respective temporary peak intensity to thereby obtain a normalized peak intensity for each of the isotopic clusters of the convoluted spectrum.

As was the case in the discussion of FIG. 5, in FIG. 9, the above order of the simultaneous intensity subtraction (940) and peak intensity addition (950) is merely illustrative of the present embodiment and should not be taken to indicate an explicit order, since the correct result would be obtained by first simultaneously adding (950) the appropriate respective peak intensities and then simultaneously subtracting (940) the appropriate respective peak intensities. In some embodiments, all additions and all subtractions are simultaneously processed (e.g., when wave function analysis is performed.) Regardless of the order of processing, the results can be stored (960) for future output and/or can be immediately output and the method can terminate. In accordance with some embodiments of the present invention, a matrix structure, for example, a 40 by 40 matrix, can be used to perform the subtractions (840) and additions (850) and to store (880) the results.

Figure 10:
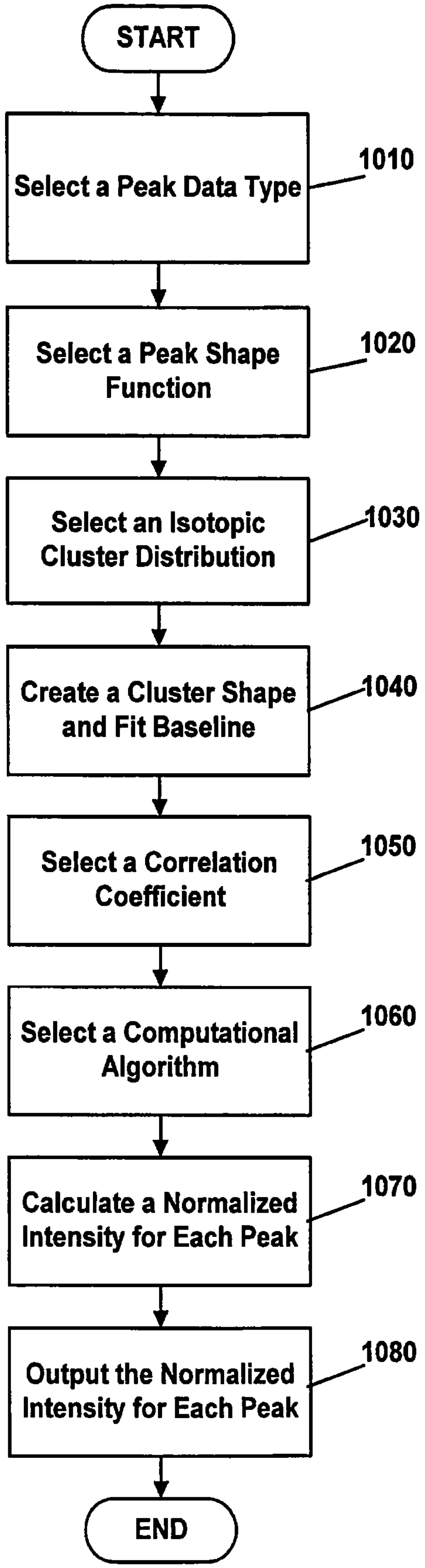
FIG. 10 is a top-level flow diagram of yet another method embodiment for de-convoluting intensity information in a convoluted spectrum.

FIG. 10 is a top-level flow diagram of a method embodiment for de-convoluting intensity information in a convoluted spectrum according to wave function analysis. The method can be used, for example, to de-convolute the convoluted spectrum of overlapping isotopic clusters illustrated in FIG. 1 or 3. In FIG. 10, the data type of known peak data intensity information to be input can be selected (1010) as being, for example, a peak list or output data, generally in an x,y plot format where the x values represent the mass or mass-to-charge ratio and the y values represent the intensity for each x value. The peak list or output data for each isotopic cluster can, for example, include ratio information on the relative abundance of each peak in the isotopic cluster and can be generated by mass analysis of a sample, or fraction thereof. The peak list can be used to generate a convoluted spectrum. A peak shape function to be used to analyze the known peak data intensity information can be selected (1020). For example, the peak shape function can be a Kreniger function, a Gauss function, a Lorentz function or a Dirac delta function. A type of the isotopic cluster distribution can be selected (1030) to describe the known isotopic cluster intensity information to be, for example, calculated or experimentally determined. The order of the initial selections (1010), (1020) and (1030) should not be construed to indicate a specific order in the method as each can occur before or simultaneously with each of the others. A baseline cluster shape for the known isotopic cluster intensity information can be created (1040) using the input peak data, selected (1010) peak data type, the selected (1020) peak shape function and the selected (1030) isotopic cluster distribution. A correlation coefficient can be selected (1050) to be used to determine the confidence level of the fit of summary peaks in a convoluted spectrum to the baseline cluster shape. A computational algorithm can be selected (1060) to be used to calculate a normalized peak intensity for each summary peak. For example, the computational algorithm can be selected (1060) from a Gauss-Newton algorithm, a Simplex algorithm, a Genetic algorithm, a lower-upper (LU) decomposition algorithm, and a SVD algorithm. A normalized peak intensity can be calculated (1070) for each summary isotope peak in the convoluted spectrum using the selected (1060) computational algorithm, the selected (1050) correlation coefficient, and the created (1040) baseline cluster shape for the known isotopic cluster intensity information. The normalized peak intensity can be output (1080) for each main summary isotope peak in the convoluted spectrum and the method may terminate.

Figure 11:
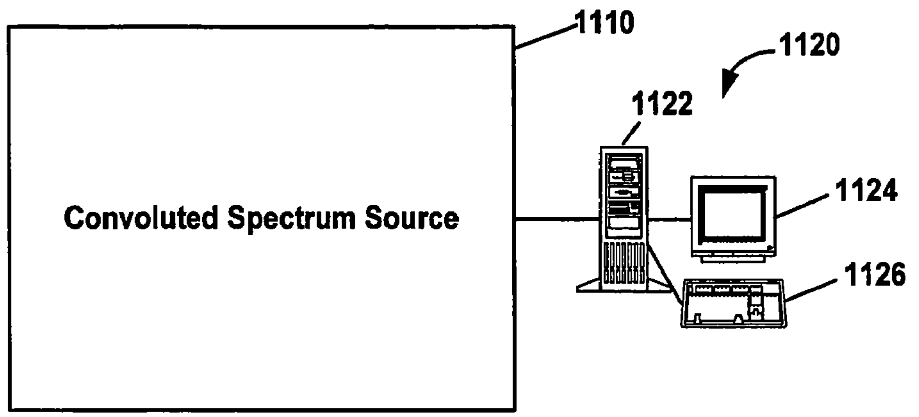
FIG. 11 is a block diagram of a system in which embodiments of the present invention can be practiced.

FIG. 11 is a block diagram of a system in which some embodiments of the present invention can be practiced. In FIG. 11, a convoluted spectrum source 1110 can be coupled to a computer system 1120. Convoluted spectrum source 1110 can include, but not be limited to, for example, a mass spectrometer (MS), a MS/MS, a quadropole MS, as well as data files from historical MS analyses. Computer system 1120 can include a processing unit 1122 coupled to a display 1124 and an input device 1126, for example, a keyboard. Other input devices 1126 can include, but are not limited to, an electronic writing tablet, a mouse, a voice activated input device, etc. Processing unit 1122 can include a processor, for example, a microprocessor or multiple processors, coupled to a memory and a mass storage device. For example, while in no way intended to limit the possible configurations of processing unit 1122, the processor can include a microprocessor, the memory can include a random access memory (RAM) and the mass storage device can include a hard disk device. Computer system 1120 can receive convoluted spectrum data and/or known isotopic cluster information (e.g., ratio information) from convoluted spectrum source 1110 and can de-convolute the convoluted spectrum data using the known isotopic cluster information, in accordance with various embodiments of the present invention.

Figure 12:
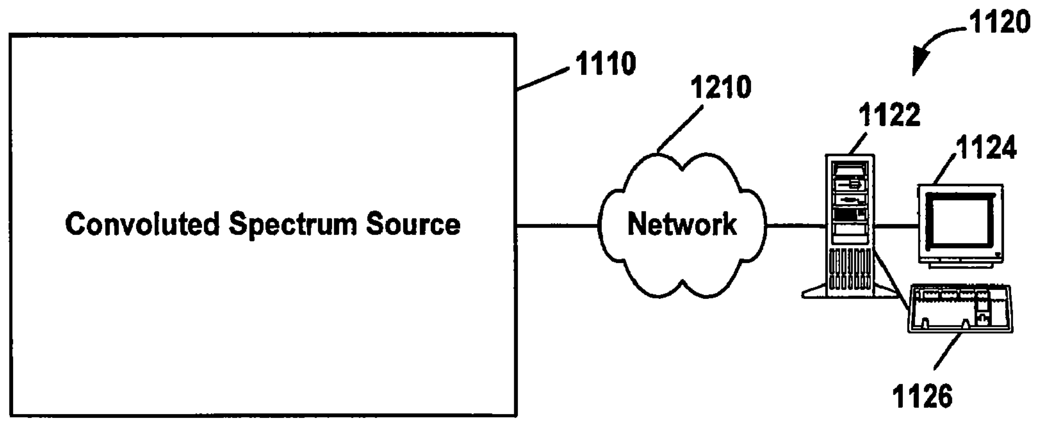
FIG. 12 is a block diagram of another system in which embodiments of the present invention can be practiced.

FIG. 12 is a block diagram of another system in which some embodiments of the present invention can be practiced. In FIG. 12, convoluted spectrum source 1110 and computer system 1120 from FIG. 11 can be coupled, in FIG. 12, via a network 1210, for example, a communications network, the Internet, a local area network (LAN), a wide area network (WAN) and a wireless network. The operation of the system in FIG. 12, as well as similar components, are identical to the system in FIG. 11 with the exception that communication of information from convoluted spectrum source 1110 to computer system 1120 can occur through network 1210.

Figure 13:
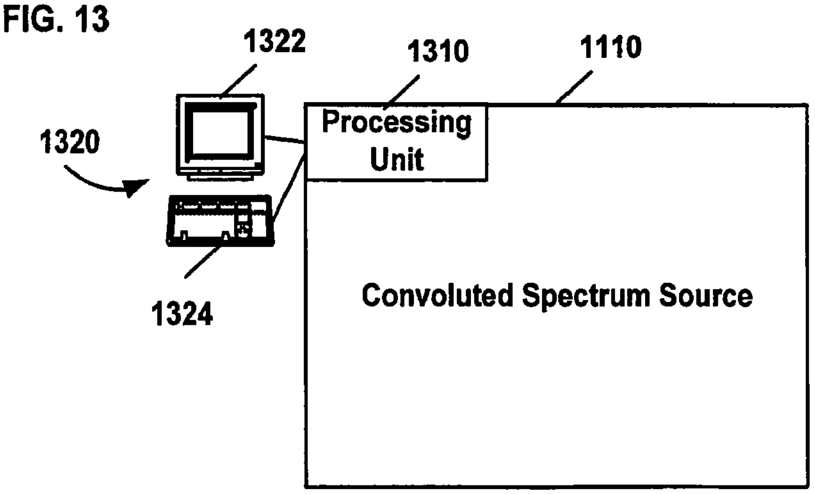
FIG. 13 is a block diagram of yet another system in which embodiments of the present invention can be practiced.

FIG. 13 is a block diagram of yet another system in which embodiments of the present invention can be practiced. In FIG. 13, convoluted spectrum source 1110 can include a processing unit 1310 that can be coupled to a peripheral subsystem 1320 including, for example, display device 1322 and input device 1324. Processing unit 1310 can be configured as described above in FIG. 11 for processing unit 1110. The operation of the system in FIG. 13, as well as similar components, are identical to the system in FIG. 11 with the exception that processing unit 1310 is located in convoluted spectrum source 1110.

Although the present invention has been disclosed in detail, it should be understood that various changes, substitutions, and alterations can be made herein. Moreover, although software and hardware are described to control certain functions, such functions can be performed using either software, hardware or a combination of software and hardware, as is well known in the art. Other examples are readily ascertainable by one skilled in the art and can be made without departing from the spirit and scope of the present invention as defined by the following claims.

What is claimed is:

1. A method comprising:

performing a survey scan to determine a mass of one or more labeled analytes, or one or more labeled fragments thereof;

selecting one of the labeled analytes or labeled fragments;

subjecting the selected labeled analyte or labeled fragment to dissociative energy levels to thereby fragment the labeled analyte or labeled fragment;

performing a single energy scan of the fragmented labeled analyte or labeled fragment; and receiving a single spectrum from the single energy scan of the fragmented analyte or fragment, the single spectrum including intensity peaks for one or more reporter ions and one or more daughter fragment ions of the selected labeled analyte or labeled fragment.

2. The method of claim 1 wherein the peaks associated with the reporter ion or ions are located in a quiet region of the spectrum.

3. The method of claim 1 wherein the reporter ions produce a convoluted spectrum of overlapping isotopic clusters associated with two or more different isotopic labeling reagents.

4. The method of claim 3 further comprising:

de-convoluting the convoluted spectrum to obtain a normalized peak intensity for each isotopic cluster in the convoluted spectrum.

5. The method of claim 4, further comprising:

determining the relative quantity of each different isotopic labeling reagent by comparing the normalized peak intensity of each isotopic cluster in the convoluted spectrum.

6. The method of claim 4 wherein de-convoluting the convoluted spectrum comprises:

de-convoluting the convoluted spectrum by removing known intensity contributions of all up-mass daughter fragment ions associated with lower mass intensity peaks for each reporter ion and all down-mass daughter fragment ions associated with higher mass intensity peaks for each reporter ion from and adding the known intensity contributions of at least one up-mass daughter fragment ion and at least one down-mass daughter fragment ion associated with each main summary intensity peak for each reporter ion to thereby obtain the normalized peak intensity for each isotopic cluster in the convoluted spectrum.

7. The method of claim 4 wherein de-convoluting the convoluted spectrum comprises:

determining a main summary isotope peak associated with each isotopic cluster; using the individual component isotope peak intensity distributions to determine known peak intensities for each of the main summary isotope peaks and the one or more up-mass side peaks and down-mass side peaks associated with the main summary isotope peak for each isotopic cluster; and removing the known intensity contributions of at least one up-mass component associated with a lower mass isotope peak and at least one down-mass component associated with a higher mass isotope peak and adding the known intensity contributions of at least one up-mass component and at least one down-mass component associated with each main summary isotope peak to thereby obtain the normalized peak intensity for each isotopic cluster.

8. A machine-readable medium having stored thereon a plurality of executable instructions to perform a method comprising:

performing a survey scan to determine a mass of one or more labeled analytes, or one or more labeled fragments thereof;

selecting one of the labeled analytes or labeled fragments;

subjecting the selected labeled analyte or labeled fragment to dissociative energy levels to thereby fragment the labeled analyte or labeled fragment;

performing a single energy scan of the fragmented labeled analyte or labeled fragment; and receiving a single spectrum from the single energy scan of the fragmented analyte or fragment, the single spectrum including intensity peaks for one or more reporter ions and one or more daughter fragment ions of the selected labeled analyte or labeled fragment.

9. The machine-readable medium of claim 8 wherein the peaks associated with the reporter ion or ions are located in a quiet region of the spectrum.

10. The machine-readable medium of claim 8 wherein the reporter ions produce a convoluted spectrum of overlapping isotopic clusters associated with two or more different isotopic labeling reagents.

11. The machine-readable medium of claim 10 wherein the method further comprises:

de-convoluting the convoluted spectrum to obtain a normalized peak intensity for each isotopic cluster in the convoluted spectrum.

12. The machine-readable medium of claim 11 wherein the method further comprises:

determining the relative quantity of each different isotopic labeling reagent by comparing the normalized peak intensity of each isotopic cluster in the convoluted spectrum.

13. The machine-readable medium of claim 11 wherein de-convoluting the convoluted spectrum comprises:

de-convoluting the convoluted spectrum by removing known intensity contributions of all up-mass daughter fragment ions associated with lower mass intensity peaks for each reporter ion and all down-mass daughter fragment ions associated with higher mass intensity peaks for each reporter ion from and adding the known intensity contributions of at least one up-mass daughter fragment ion and at least one down-mass daughter fragment ion associated with each main summary intensity peak for each reporter ion to thereby obtain the normalized peak intensity for each isotopic cluster in the convoluted spectrum.

14. The machine-readable medium of claim 11 wherein de-convoluting the convoluted spectrum comprises:

determining a main summary isotope peak associated with each isotopic cluster; using the individual component isotope peak intensity distributions to determine known peak intensities for each of the main summary isotope peaks and the one or more up-mass side peaks and down-mass side peaks associated with the main summary isotope peak for each isotopic cluster; and removing the known intensity contributions of at least one up-mass component associated with a lower mass isotope peak and at least one down-mass component associated with a higher mass isotope peak and adding the known intensity contributions of at least one up-mass component and at least one down-mass component associated with each main summary isotope peak to thereby obtain the normalized peak intensity for each isotopic cluster.

15. A computer system comprising:

a processor; and a memory coupled to the processor, and the memory having stored thereon a plurality of executable instructions to perform a method including:

performing a survey scan to determine a mass of one or more labeled analytes, or one or more labeled fragments thereof;

selecting one of the labeled analytes or labeled fragments;

subjecting the selected labeled analyte or labeled fragment to dissociative energy levels to thereby fragment the labeled analyte or labeled fragment;

performing a single energy scan of the fragmented labeled analyte or labeled fragment; and receiving a single spectrum from the single energy scan of the fragmented analyte or fragment, the single spectrum including intensity peaks for one or more reporter ions and one or more daughter fragment ions of the selected labeled analyte or labeled fragment.

16. The computer system of claim 15 wherein the memory has an additional plurality of executable instructions to perform another method including:

receiving the single spectrum as a convoluted spectrum for a group of overlapping isotopic clusters;

determining a normalized peak intensity for a main summary isotope peak in said convoluted spectrum for each of a plurality of main summary isotope peaks in the convoluted spectrum by, for each main summary isotope peak, subtracting known intensity contributions for at least one lower mass isotope cluster up-mass side peak and at least one higher mass isotope cluster down-mass side peak from and adding known intensity contributions for at least one down-mass side peak and at least one up-mass side peak of the isotopic cluster to the respective main summary isotope peak; and storing said normalized peak intensity for each of said plurality of main summary isotope peaks wherein each normalized peak intensity represents a different isotopic cluster of the group of overlapping isotopic clusters.

17. The computer system of claim 15 further comprising:

an input device coupled to the processor; and a display device coupled to the processor.

18. The computer system of claim 15 wherein the processor comprises at least one microprocessor.

19. The computer system of claim 15 wherein the processor is directly coupled to the convoluted spectrum source.

20. The computer system of claim 15 wherein the processor is coupled to the convoluted spectrum source via a network.

21. The computer system of claim 15 wherein the processor is included in the convoluted spectrum source.

22. An apparatus comprising:

a single spectrum source;

a processor coupled to the single spectrum source; and a memory coupled to the processor, and the memory having stored thereon a first plurality of executable instructions to control the single spectrum source to perform a first method including:

performing a survey scan to determine a mass of one or more labeled analytes, or one or more labeled fragments thereof;

selecting one of the labeled analytes or labeled fragments;

subjecting the selected labeled analyte or labeled fragment to dissociative energy levels to thereby fragment the labeled analyte or labeled fragment;

performing a single energy scan of the fragmented labeled analyte or labeled fragment; and receiving a single spectrum from the single energy scan of the fragmented analyte or fragment, the single spectrum including intensity peaks for one or more reporter ions and one or more daughter fragment ions of the selected labeled analyte or labeled fragment;

the memory further having stored thereon a second plurality of executable instructions to perform a second method including:

receiving the single spectrum as a convoluted spectrum for a group of overlapping isotopic clusters;

determining a normalized peak intensity for a main summary isotope peak in said convoluted spectrum for each of a plurality of main summary isotope peaks in the convoluted spectrum by, for each main summary isotope peak, subtracting known intensity contributions for at least one lower mass isotope cluster up-mass side peak and at least one higher mass isotope cluster down-mass side peak from and adding known intensity contributions for at least one down-mass side peak and at least one up-mass side peak of the isotopic cluster to the respective main summary isotope peak; and storing said normalized peak intensity for each of said plurality of main summary isotope peaks wherein each normalized peak intensity represents a different isotopic cluster of the group of overlapping isotopic clusters.

23. The apparatus of claim 22 wherein said single spectrum source comprises:

a tandem mass spectrometer/mass spectrometer (MS/MS).

24. The apparatus of claim 23 further comprising:

an input device coupled to the processor; and a display device coupled to the processor.

25. The apparatus of claim 24 wherein the processor comprises at least one microprocessor.

26. The apparatus of claim 25 wherein the processor is directly coupled to the convoluted spectrum source.

27. The apparatus of claim 25 wherein the processor is coupled to the convoluted spectrum source via a network.

28. The apparatus of claim 25 wherein the processor is included in the convoluted spectrum source.

* * * * *

UNITED STATES PATENT AND TRADEMARK OFFICE

CERTIFICATE OF CORRECTION

PATENT NO. : 7,309,858 B2
APPLICATION NO. : 11/458082
DATED : December 18, 2007
INVENTOR(S) : Darryl J. C. Pappin et al.

It is certified that error appears in the above-identified patent and that said Letters Patent is hereby corrected as shown below:

Claim 1, Column 19, line 31, please replace the words “a single” with --an--

Claim 1, Column 19, line 33, please replace the word “single” from before the word “spectrum”

Claim 1, Column 19, line 33, please remove the word “single” from in front of the words “energy”

Claim 1, Column 19, line 34, please remove the word “single”

Claim 8, Column 20, line 29, please replace the words “a single” with --an--

Claim 8, Column 20, line 31, please remove the words “single” from in front of the words “spectrum” and “energy”

Claim 8, Column 20, line 32, please remove the word “single”

Claim 15, Column 21, line 23, please replace the word “including” with --comprising--

Claim 15, Column 21, line 31, please replace the words “a single” with --an--

Claim 15, Column 21, line 34, please remove the words “single” from before “spectrum” and “energy”

Claim 15, Column 21, line 35, please remove the word “single”

Claim 16, Column 21, line 41, please replace the word “including” with --comprising--

Claim 16, Column 21, line 42, please remove the word “single”

Claim 19, Column 21, line 66, please remove the words “the convoluted spectrum source” and replace with --a source of the spectrum--

Claim 20, Column 22, line 2, please remove the words “the convoluted” and replace with --a source of the--

Claim 20, Column 22, line 2, please remove the word “source”

Claim 21, Column 22, line 5, please remove the words “the convoluted” and replace with --a source of the--

UNITED STATES PATENT AND TRADEMARK OFFICE

CERTIFICATE OF CORRECTION

PATENT NO. : 7,309,858 B2
APPLICATION NO. : 11/458082
DATED : December 18, 2007
INVENTOR(S) : Darryl J. C. Pappin et al.

It is certified that error appears in the above-identified patent and that said Letters Patent is hereby corrected as shown below:

Claim 21, Column 22, line 5, please remove the word “source”

Claim 22, Column 22, line 7, please remove the word “single”

Claim 22, Column 22, line 12, please replace the word “including” with --comprising--

Claim 22, Column 22, line 21, please replace the words “a single” with --an--

Claim 22, Column 22, line 23, please remove the word “single” from in front of the words “spectrum” and “energy”

Claim 22, Column 22, line 24, please remove the word “single”

Claim 22, Column 22, line 30, please replace the word “including” with --comprising--

Claim 22, Column 22, line 31, please remove the word “single”

Claim 23, Column 22, line 50, please remove the word “single”

Claim 26, Column 22, line 60, please remove the word “convoluted”

Claim 27, Column 22, line 62, please remove the word “convoluted”

Claim 28, Column 22, line 64, please remove the word “convoluted”

Signed and Sealed this

Sixth Day of January, 2009

Jon W. Dudas

JON W. DUDAS
*Director of the United States Patent and Trademark Office*